US012773572B2

(12) United States Patent
Wegdam et al.

(10) Patent No.: US 12,773,572 B2
(45) **Date of Patent: *Oct. 27, 2026**

(54) DEVICE FOR RADIATING UV AND/OR IR RADIATION TO A HUMAN BODY IN A HUMID ROOM

(71) Applicant: Sunshower IP BV, Amsterdam (NL)

(72) Inventors: Pieter Merijn Wegdam, Amsterdam (NL); Wiebe Jelmer Koehler, Amsterdam (NL)

(73) Assignee: Sunshower IP BV, Amsterdam (NL)

( * ) Notice: Subject to any disclaimer, the term of this patent is extended or adjusted under 35 U.S.C. 154(b) by 211 days.

This patent is subject to a terminal disclaimer.

(21) Appl. No.: 18/721,605

(22) PCT Filed: Dec. 21, 2022

(86) PCT No.: PCT/NL2022/050741

§ 371 (c)(1),
(2) Date: Jun. 18, 2024

(87) PCT Pub. No.: WO2023/121451

PCT Pub. Date: Jun. 29, 2023

(65) Prior Publication Data

US 2025/0090856 A1 Mar. 20, 2025

(30) Foreign Application Priority Data

Dec. 24, 2021 (NL) ..................................... 2030285

(51) Int. Cl.
*A61N 5/06* (2006.01)

(52) U.S. Cl.
CPC ...... *A61N 5/0614* (2013.01); *A61N 2005/064* (2013.01); *A61N 2005/0659* (2013.01);
(Continued)

(58) Field of Classification Search
None
See application file for complete search history.

(56) References Cited

U.S. PATENT DOCUMENTS

| | | | | |
|---|---|---|---|---|
| 4,130,120 A * | 12/1978 | Kohler, Jr. | A61N 5/0614 | 607/80 |
| 5,892,619 A * | 4/1999 | Chubb | A41D 1/00 | 49/404 |

(Continued)

FOREIGN PATENT DOCUMENTS

| | | |
|---|---|---|
| DE | 9412233 U1 | 9/1994 |
| EP | 3251725 A1 | 12/2017 |

(Continued)

OTHER PUBLICATIONS

Search Report and Written Opinion for The Netherlands Patent Application No. NL2030285, completed Aug. 5, 2022.

(Continued)

*Primary Examiner* — Michael T. Holtzclaw
(74) *Attorney, Agent, or Firm* — Andrus Intellectual Property Law, LLP

(57) ABSTRACT

The invention relates to a device for radiating UV and/or IR radiation to a human body, in particular for use in a humid room, such as a bathroom. The invention further relates to a housing intended for use in such a device for radiating UV and/or IR radiation to a human body, in particular for use in a humid room, such as a bathroom.

20 Claims, 12 Drawing Sheets

(52) U.S. Cl.
CPC ................. *A61N 2005/0661* (2013.01); *A61N 2005/0666* (2013.01); *A61N 2005/0668* (2013.01)

(56) References Cited

U.S. PATENT DOCUMENTS

| | | | | |
|---|---|---|---|---|
| 9,950,136 | B2 * | 4/2018 | Jedrzejewski ....... | A61N 5/0614 |
| 2003/0078635 | A1 | 4/2003 | Ullrich et al. | |

FOREIGN PATENT DOCUMENTS

| | | | | |
|---|---|---|---|---|
| KR | 200388141 | Y1 * | 6/2005 | ............... A47K 3/10 |
| WO | 2004004830 | A1 | 1/2004 | |
| WO | 2008140315 | A1 | 11/2008 | |

OTHER PUBLICATIONS

International Search Report and Written Opinion for International Patent Application No. PCT/NL2022/050741, mailed Mar. 13, 2023.

* cited by examiner

DEVICE FOR RADIATING UV AND/OR IR RADIATION TO A HUMAN BODY IN A HUMID ROOM

CROSS-REFERENCE TO RELATED APPLICATIONS

This is a national stage application filed under 37 U.S.C. 371 based on International Patent Application No. PCT/NL2022/050741, filed on Dec. 21, 2022, which claims priority to Netherlands Patent Application No. 2030285, filed on Dec. 24, 2021, the disclosures of which are incorporated herein by reference in their entireties.

The invention relates to a device for radiating ultraviolet (UV) and/or infrared (IR) radiation to a human body, in particular for use in a humid room, such as a bathroom. The invention further relates to a housing for use in a device according to the invention. The invention also relates to an assembly for use in a device according to the invention, said assembly comprising a radiation transmitting wall and a support frame, directly or indirectly, attached to a rear side of said wall.

In the short history of artificial bronzing one of the greatest changes we could notice was the proportional increase in sun showers, as for example disclosed in WO2004/004830, to the detriment of sun beds. A sun shower is installed in upright position in a humid room, such as a bathroom, and has brought many advantages, like more controlling tanning times, a saving of space and time, and an improved hygiene during tanning. However, the sun shower can be relatively heavy which renders the installation rather difficult and laborious.

It is therefore an object of the present invention to provide an improved sun shower device which can be installed in a user-friendly manner.

It is therefore another object of the present invention to provide an improved sun shower device which can be serviced in an improved manner.

One of these objects can be achieved by providing a device according to the preamble, comprising:

- a housing, preferably an upright housing, comprising a circumferential wall and a rear wall connected to said circumferential wall, wherein said upright housing defines an accommodating space,
- at least one radiation unit accommodated within said accommodating space, wherein each radiation unit comprises at least one radiation source for radiating UV and/or IR radiation, and at least one reflector,
- at least one radiation transmitting wall to close, in particular seal, the accommodating space at least partially, wherein opposing inner surfaces of the circumferential wall are provided with support elements, and wherein said radiation transmitting wall is provided with a support frame, directly or indirectly, attached to a rear side of said radiation transmitting wall, wherein said support frame comprises a plurality of slots configured to co-act with the support elements of the housing for mounting the radiation transmitting wall to the housing.

The modular construction of the device according to the invention allows a step by step installation of the device, wherein firstly the housing can be mounted to a wall, after which the one or more radiation units can be mounted within said housing, followed by closing off the housing by attaching the wall to the housing. This improves the user friendliness of the installation significantly, and is less laborious with less risk of damage. Moreover, the wall can be releasably connected to the housing, which means that the wall can be removed from the housing in case electronic components accommodated within the housing should be serviced. Preferably, the frame and radiation transmitting wall are connectable to the housing in a self-guiding manner. That is, the plurality of slots in the frame together with the support elements mutually allow the frame and the wall to be guided in a stably suspended position. Therefore, it is particularly preferred that the support elements are part of the housing of the device, preferably rigidly connected to said housing. As such, the support elements may provide for a rigid anchoring of the frame and radiation transmitting wall to the device. Preferably, the frame comprises at least one, preferably two, contact surface, which is in contact with the rear side of the radiation transmitting wall when the latter two are coupled. Said contact surfaces preferably stretch over a portion of the height of the frame, preferably over at least 50 percent of the height of the frame, more preferably at least 75 percent, in particular at least along 85 percent of the length of the frame. This allows for a strong attachment of the frame to the rear of the radiation transmitting wall. In particular since the temperature of the device may fluctuate a lot.

In respect of the present invention, the front is understood to be the side of the device comprising the radiation transmitting wall. This side will face towards a user and allow a user to be radiated by the UV and/or IR light. The back is understood as the side of the device facing away from the radiation transmitting wall, typically the side that is built into a wall during installation of the device. The depth of the device extends thus in a direction from front to back (or back to front). Hence, the rear wall of the housing may form part of the back of the device. The height may be understood in this application as the direction of the longitudinal axis of the device or the upright housing as such. The width direction, hence, is orthogonal to both the height and the depth of the device. This may as such be defined as left to right.

Preferably, a bottom part of the housing comprises and/or accommodates at least one securing element for locking in place the radiation transmitting wall when connected to the housing, in particular to the circumferential wall of the housing, more in particular to the support elements of the circumferential wall of the housing. Preferably, the securing element is movably mounted onto a stationary support structure, more preferably such that the securing element is configured to slide over a restricted distance in vertical direction between an unlocked state and a locked state. Preferably, the securing element is movably mounted, in particular slidably mounted, onto the stationary support structure such that the support structure secures the securing element which prevents accidental release of the securing element with respect to the support structure. Preferably the securing element is a, preferably elongated, securing element which comprises a visual indicator which is visible for a user in the unlocked state, which is preferably the lowest position of the securing element, and which is invisible for a user in the locked state, which is preferably a higher position, more preferably the highest position, of the securing element. Typically, the radiation transmitting wall at least partially covers the securing element, wherein, preferably, the wall entirely covers the securing element in locked state (as seen from a front view of the device), and partially covers the securing element in an unlocked state, wherein the visual indicator will be left uncovered by the wall and hence visible for a user. In this manner, the user is given a visual warning when the securing element is positioned in an unlocked state, and hence the wall is mounted to the housing in an unlocked manner. To this end, the visual indicator may e.g. comprise a text such as "OPEN" and/or show a red coloured surface. The securing element preferably comprises at least one spring which, in locked condition, locks the radiation transmitting wall in place with respect to the housing, and wherein said radiation transmitting wall can be unlocked with respect to the housing by manually pressing said spring into an unlocking state. After unlocking the securing element can be slid towards the unlocked state, preferably by using gravitational forces. Preferably, the spring is accessible via a (small) opening present in the bottom part of the bottom housing segment and/or in a bottom part of the securing element. The securing element is preferably made of one piece of material, preferably polymer material. A middle section of the securing element may be provided with guiding means for guiding a tool, such as screw driver or other pin, to manually operate the spring, in particular to manually move the spring from a locked state to an unlocked state, in order to unlock the securing element which results in unlocking the wall with respect to the housing.

In a preferred embodiment, opposing inner surfaces of the circumferential wall of the housing are provided with support elements for, directly or indirectly, supporting at least one wall, preferably an outer wall. Each of these support elements may, for example, be is formed by a protruding pin which protrudes, preferably inwardly protrudes, with respect to the inner surface of the circumferential wall. Hence, preferably, a terminal end surface of such an inwardly protruding pin faces an opposing inner surface of the circumferential wall. It is imaginable, and even preferable, that opposing inner surfaces of the circumferential wall have a mutually tapered (converging) orientation, wherein the distance between said opposing inner surfaces preferably decreases in a direction away from the radiation transmitting wall (hence in backward direction). This tapered orientation facilitates installation, in particular placement, of the device into a wall opening of a wall of e.g. a shower (cubicle). The aforementioned preferably inwardly protruding pins preferably extend in a direction which is substantially parallel to a plane defined by the radiation transmitting wall. This typically facilitates installation, in particular mounting of the radiation transmitting wall, to the upright housing. More in particular such an orientation facilitates coupling of the slots with respect to the pins, respectively, as these pins are typically configured to co-act with slots present in a support frame (or support rail(s)), directly or indirectly, attached to a rear side of the radiation transmitting wall. These slots a preferably arranged in opposing vertical parts, in particular side walls, of the support frame. This allows the radiation transmitting wall to be supported by and to be hung (mounted) onto the inwardly protruding pins. Due to gravitational forces, this orientation of the slots (and pins) typically leads to a self-locking effect. This prevents accidental release of the radiation transmitting wall. The slots are preferably non-linear. Preferably, each slot comprises an upwardly inclined inlet section and upright end section connecting to said inclined inlet section, wherein, preferably, an angle enclosed by a central axis of the inclined inlet section and a vertical axis is situated between 15 and 75 degrees, more preferably between 45 and 65 degrees. Here, the lowest level of the slot is typically defined by an access opening of the inlet section. Preferably the maximum width of the inlet section exceeds the maximum width of the end section. This allows the inlet section to act as guiding section to guide an aforementioned pin towards the end section. In this manner, the installation of the wall can be facilitated significantly. Moreover, this results in a self-locking mechanism as the wall will be locked by the slots and support elements and will be kept in place due to gravitational forces. Preferably, at least one slot, preferably all slots comprises at least a part which extend substantially vertical. Preferably, an end section of at least one, preferably all slots is substantially vertical. This may contribute to a stable connection between housing and radiation transmitting wall in coupled condition of the two. Preferably the width of the end section substantially corresponds to the outer diameter of a corresponding pin. The distance between adjacent support elements, in particular pins, is preferably constant to facilitate installation of the (outer) radiation transmitting wall. The support frame and/or support rail(s) is, either directly or indirectly, attached to a radiation transmitting wall (or plate). The support frame is preferably at least partially made of a polymer and/or a metal. Preferably, the support frame leaves the at least one radiation unit substantially uncovered. Preferably, the radiation transmitting wall extends beyond the support frame and/or support rail(s) and therefore covers the support frame and/or support rail(s). Preferably, radiation transmitting wall is formed by a glass plate, wherein said support frame is attached to a rear side of said cover plate. Said cover plate typically defines a front surface of the device which is exposed to the humid room and to the user. It is imaginable and even favourable in case at least one radiation transmitting wall has a transparent center section and a less transparent or untransparent edge section. This allows the support frame and/or support rail(s), and optionally other mechanical components to be hidden from the outside.

Preferably, each of said opposing inner surfaces of the circumferential wall provided with support elements, is provided with a plurality of support elements. Preferably, each part of the support frame configured to co-act with said plurality of support elements arranged at the same inner surface of the circumferential wall comprises a plurality of slots. Applying a plurality of support elements and slots per side increases the load capacity of the device, which makes the device less vulnerable and more robust. Preferably, the number of support elements is identical to the number of slots, in particular per side of the device (e.g. the left side and the right side).

Preferably, at least one radiation transmitting wall, in particular the inner radiation transmitting wall, is attached to the frame by means of at least one attaching element. Preferably, said inner radiation transmitting element is affixed to the frame through a plurality of separate attaching elements. Using separate attaching elements, preferably each at a mutual distance, allows to reduce the tension in the attaching element, as compared to a single elongated attaching element which spans along a significant part of the radiation transmitting wall. Preferably, at least one attaching element, preferably all, is formed by a clamp. Preferably the attaching element is provided with at least one hole, said hole dimensioned such that a threaded part of a pin protruding from the frame may pass through said clamp for clamping of the radiation transmitting wall. The clamping force may be adjusted by tightening or untightening a nut. It is preferred, to this end, that the frame comprises a plurality of protruding pins, each comprising a threaded section. Additionally, the radiation transmitting wall may be provided with holes, which holes are aligned with the protruding pins. This allows the pins to pass through the holes of the wall. To fasten the wall, the aforementioned clamps may be utilized. It is imaginable that the frame comprises at least one stress relieving element. Due to the high range of temperatures of the device, materials used are subjected to large temperature variations. Since the frame attached on the rear side of the radiation transmitting wall and the radiation transmitting wall itself are made out different materials, one may expand or contract more compared to the other due to temperature fluctuations, in particular when being heated. This causes mutual stress which may result into the frame to warp as a result of the stresses. Since said frame is, in coupled condition, connected to the housing, the housing may also be subjected to some degree of warping. At least one stress reliving element may contribute to reduce the amount of warping. Preferably, said stress relieving element is formed by at least one notch and/or slit in said frame. Said notch and/or slit preferably extends at least in a lateral direction of the frame. It is preferred that said notch and/or slit does not extend all the way, separating the frame in two parts, since this affects the stiffness of the frame significantly in a negative way. Therefore, it is preferred that parts of the frame adjacent to the notch and/or slit remain at least partially attached. It was found that a notch or slit having a width of about 1.0 mm to 2.0 mm, in particular 1.5 mm was sufficient to alleviate the warping of the frame as a result to temperature fluctuations, whilst preventing a significant loss of cooling performance due to air leakage.

Preferably, at least one of the inner radiation transmitting wall or outer radiation transmitting wall is larger compared to the other. Preferably, at least one of the inner radiation transmitting wall or the outer radiation transmitting wall rests, in coupled condition, on an edge of the circumferential wall of the housing. Preferably, said outer radiation transmitting wall rests, in coupled condition, at least partially on the edge of the circumferential wall of the housing. In particular, at least one of the inner radiation transmitting wall or the outer radiation transmitting wall rests, in coupled condition, on an edge of the circumferential wall of the housing and the other is arranged within the circumferential wall of the housing. This may be possible through the frame, which may hold the inner and outer radiation transmitting walls at a mutual distance.

Preferably, the device according to the invention comprises a modular housing composed of intercouplable housing segments. This feature provides flexibility in design and dimensioning of the housing, which facilitates to tailor the design, in particular the dimensioning, of the housing, and hence of the device as such, to the specific circumstances, such as the design of the (humid) room where the device will be applied and/or the desires of the end-consumer to go for a larger (longer) or smaller (shorter) device.

The coupling profiles are typically used to mutually connect adjacent housing segment, preferably in a watertight manner, to prevent (shower) water and moisture to enter into the housing. Realizing a substantially watertight seal, preferably with a minimum IPX-rating of IPX-5 (the waterproof connection can resist a sustained, low-pressure water jet spray), as defined in international standard IEC 60529, between the housing segments is preferred due to the electronic equipment housed in the accommodating space of the housing. Typically the circumferential wall segment and the rear wall segment of a housing segment are integrally connected out of one piece of material. In this case each housing segment constitutes a shell segment for composing a shell constituted by the housing. Preferably, the housing segment is at least partially made of a (co)polymeric material, preferably a thermoplastic (co)polymeric material. Preferably, the (co)polymeric material is enriched with at least one flame retardant to reduce the flammability of the housing, which is in favour of the safety of the device. Preferably, a relatively temperature resistant (co)polymeric material or blend of (co)polymeric materials is used. To this end, it is preferred that the Vicat softening temperature of the housing is at least 80° C., preferably at least 90° C., and more preferably at least 100° C. as measured according to B120 method as defined in ISO306.

Preferably, each housing segment is provided with at least two support elements located at opposing and facing inner surfaces of the circumferential wall segment of said housing segment. This secures that each housing segment will contribute to the support of the wall.

The housing is preferably an upright housing, which means that the housing has a substantially vertical longitudinal axis. Since the device is commonly encased in a humid room, in particular in or adjacent to a shower space, the human body can be irradiated from top to bottom while standing in said shower space. This vertical orientation of the housing implies that the housing at least comprises a bottom housing segment and a top housing segment. Although different bottom housing segments with mutually different dimensions can be used, and the same applies to the top housing segment, which would result in housings with different dimensions, it is typically preferred that a single, uniform type of bottom housing segment is used and that a single, uniform type of top housing segment is used. Each of the bottom housing segment and the top housing segment preferably comprises a circumferential wall segment which is composed of two opposing, typically vertical, walls and one lateral, typically horizontal, wall connecting to said opposing, typically vertical, walls. Applying a uniformly shaped and dimensioned bottom housing segment and top housing segment is preferable from an economic and logistic point of view. Hence, the flexibility in the size of the housing is preferably realized by using one or more intermediate housing segments. Different housing segments may have different dimensions. However, it is typically preferred from an economic and logistic point of view to use one uniform type of intermediate housing segments. Dependent on the desired size of the housing from zero to a plurality of intermediate housing segments can be selected, wherein after selecting the housing segments to compose the housing with said desired size, one or more matching radiation units and at least one matching radiation transmitting wall can be selected for constructing the device according to the invention. Hence, preferably the housing comprises one top housing segment, one bottom housing segment, and at least one intermediate housing segment situated in between with said top housing segment and said bottom housing segment. Typically, the circumferential wall of each intermediate housing segment preferably comprises of (solely) two opposing, typically vertical, walls.

In coupled condition of housing segments, the circumferential wall segments of said housing segments overlap partially, and the rear wall segments of said housing segments overlap partially. Overlapping parts of adjacent, intercoupled housing segments contribute to realize a substantially waterproof connection between the housing segments. Preferably, the partial overlap is such that the circumferential wall segment and the rear wall segment of an higher located housing segment partially encloses the circumferential wall segment and the rear wall segment of an adjacent, lower located housing segment. Such an orientation improves the water barrier properties of the coupling between housing segments. Furthermore, it is typically advantageous in case adjacent housing segments are configured to mutually engage under bias in coupled condition of said housing segments. Such a bias (tension) contributes to close the seam in between said housing segments, which is not only in favour of the waterproofness of the housing, but also firmly secures the housing segments with respect to each other, which as such leads to a firm, robust, and durable construction of the housing as such.

It is imaginable that at least one coupling profile is present at at least one coupling edge defined by both the circumferential wall segment and the rear wall segment. This coupling edge may be formed by the upper edge and/or lower edge of a housing segment. Hence, this implies that it is preferred that the housing segments are mutually coupled or connected at facing (coupling) edges of said housing segments. Coupling profiles which are configured to co-act with each other typically have a complementary shape with respect to each other. This means that typically a first coupling profile of a first housing segment will be coupled to a second coupling profile of a second housing segment. Typically, the design of the first coupling profile and the design of the second coupling profile are different, although it may be conceivable that both coupling profiles are identical in practice.

Preferably, the coupling profiles of the housing comprises a first coupling profile and a complementary second coupling profile, wherein said first coupling profile comprises at least one locking element and wherein said second coupling profile comprises at least one complementary counterlocking element, wherein, in coupled condition of adjacent housing segments, said at least one locking element and said at least one counterlocking element are configured to mutually lock said housing segments, preferably in particular both in horizontal and in vertical direction. Hence, the locking elements and counter locking elements prevent unlocking of the housing segments, and preferably secure a tight connection between the housing segments, which is substantially free of any play. This latter will typically improve that water barrier properties of the housing as such. Preferably, both the circumferential wall segment and the rear wall segment of each housing segment are provided with at least one locking element and/or at least one counterlocking element. More preferably, the first coupling profile comprises locking elements and no counterlocking elements, while the second coupling profile comprises counterlocking element and no locking elements. Preferably, the locking elements are formed by locking recesses, whereas the counterlocking elements are formed by locking protrusions configured to be accommodated within said locking recesses. Alternative locking elements and counterlocking elements as well as providing a coupling profile both with one or more locking elements and with one or more counterlocking elements are also conceivable. Preferably, at least one coupling profile is configured to be partially enclosed by an adjacent coupling profile. In this manner, at least one coupling profile or even both intercoupled coupling profiles could be hidden from the outside of the housing. This not only improves the water barrier properties of the housing, but also protects the coupling profiles against damage.

Preferably, each upwardly directed coupling profile is at least partially a male coupling profile, and wherein each downwardly directed coupling profile is at least partially a female coupling profile configured to accommodate at least a part of said coupling profile. This orientation and design of coupling profiles improves the water barrier properties of the housing segments. Preferably, each pair of intercoupled coupling profiles define a seam, wherein said seam has a non-linear cross-section. This non-linear cross-section leads to a non-linear path acting as labyrinth for water to enter the housing via the seam, which renders it more difficult for water to enter the housing. The non-linear cross-section preferably defines a step-like pattern or block-like pattern including discontinuities, such as right angles, to improve the water barrier properties. Preferably, an outer section of the seam, adjacent to the surrounding atmosphere, is located lower than at least a part of a central section or inner section of said seam, located more towards the accommodating space of the housing. This elevation of the seam, as seen from the outer section towards the inner section, makes it more difficult for water to penetrate the seam and to enter the housing.

Preferably, the coupling profiles of adjacent housing segments are configured to realize a snap connection (click connection). Such a snap connection, for example realized by co-action of the aforementioned locking elements and counterlocking elements, typically contributes to realize a rigid and reliable connection between the housing segments, which is in favour of the water barrier properties of the housing.

Optionally, at least one coupling profile of at least one housing segment may be provided with a sealing material, such as a rubber strip, to further improve the waterproof properties of the coupling of adjacent housing segments.

Preferably, the device comprises an inner radiation transmitting wall, covering the at least one radiation unit, and an outer radiation transmitting wall, covering said inner radiation transmitting wall, and connected to the circumferential wall of the housing to close, in particular seal, the accommodating space at least partially, wherein the inner radiation transmitting wall and outer radiation transmitting wall are spaced apart, and preferably are oriented mutually parallel. Typically, the radiation sources will develop a significant amount of heat during operation. By applying two radiation transmitting walls which are spaced apart and mutually typically enclose a front cooling channel (see also below), the temperature of the outer radiation transmitting wall, which is exposed to the user, can be kept limited, which prevent burns. Preferably, both the inner radiation transmitting wall and outer radiation transmitting wall are at least partially made of glass, in particular quartz glass and/or tempered glass. Glass is highly transmissive and prevents absorption of considerable amounts of radiation initially intended to be transmitted to the user. Preferably, the outer radiation transmitting wall comprises at least one sealing element to seal a circumferential space between the outer radiation transmitting wall and the housing. As mentioned above, the outer radiation transmitting wall preferably is provided with a support frame which is configured to co-act with the support elements of the housing for mounting the outer radiation transmitting wall. Typically, the inner radiation transmitting wall is attached to the one or more radiation units and/or to the housing.

Preferably, the device further comprises a cooling circuit for cooling the one or more radiation units and/or the inner radiation transmitting wall and/or outer radiation transmitting wall, which cooling circuit comprises at least one cooling channel inlet at the bottom part of the housing, at least one cooling channel outlet at the bottom part of the housing, a cooling channel connecting to both the at least one channel inlet and the at least one channel outlet, wherein said cooling channel preferably comprises: a front cooling channel, connecting to said channel inlet and extending from said channel inlet to the space enclosed by the inner radiation transmitting wall and outer radiation transmitting wall, a rear cooling channel, connected both to the front cooling channel, preferably through an interconnection part at the top side of the device, and to the channel outlet, which rear channel includes a space enclosed by the at least one radiation unit and the rear wall of the housing; at least one fan, preferably accommodated in the accommodating space of the housing, arranged to force cooling air sucked by said fan into the at least one cooling channel inlet to flow through the cooling channel and to be removed via at least one cooling channel outlet meanwhile cooling the at least one radiation unit and/or the inner radiation transmitting wall and/or outer radiation transmitting wall, wherein the at least one cooling channel inlet and the at least one cooling channel outlet are preferably aligned (arranged side by side) in width direction of the housing. The lateral alignment of the housing is also referred to as a side by side orientation of the at least one channel inlet and the at least one channel outlet, in width direction of the housing, and hence as seen from the left to the right (or vice versa) seen from a front view of the device. By applying this sideward orientation of the inlet(s) and outlet(s), merely a compact section, and preferably a front section, of the bottom part of the housing can be provided with the inlet(s) and outlet(s), which allows a remaining section of the bottom part of the housing and its section located above this remaining section to be encased in a wall of a (humid) room. In this manner, the installation depth of the device can be increased significantly, while preserving a reliable and sufficient cooling of the device, in particular of the radiation source(s) during operation.

The fan, preferably a radial fan, is preferably positioned within the accommodating space of the housing, and may be positioned near to a channel inlet and/or channel outlet. Preferably, at least one fan, and more preferably each fan, is mounted within the housing by using one or more vibration damping mounting elements, such as rubber plugs, which will be in favour of the noise production of the device as such. Preferably, the fan is positioned near the channel inlet, as this creates positive air pressure within the housing, which reduces “dead spots” in the housing and prevents dust from coming in through the seams of the housing during operation of the fan.

Preferably, the device comprises at least one controller to control the one or more radiation sources and/or one or more fans. Preferably, the controller is programmed to adjust the fan speed during operation of the device. More preferably, the device comprises at least temperature sensor which is connected to the controller, and wherein the controller is programmed to adjust the fan speed dependent on the detected temperature. For example, in case the initial temperature in the housing is below a critical value, the fan speed is adjusted to 75% of the regular fan speed. In case of higher initial temperatures, the fan speed may be increased to higher levels. Moreover, the temperature sensor may be used to turn of the device in case of a temperature exceeding a predetermined value. It is also conceivable that the controller is programmed to adjust the fan speed dependent on how long the device is turned on, or how long the device was turned on prior to a current usage. In accordance with said time, a pulse width modulation signal may be adapted. After use of the device, wherein the radiation source(s) is/are switched off by the controller, a certain fan speed may be maintained for a predefined period of time and/or until the temperature within the housing drops below a predefined value.

Preferably, the cooling circuit comprises at least one protective valve to close the channel inlet and/or the channel outlet when the fan is off, and/or to open the channel inlet and the channel outlet when the fan is on. Preferably, each channel inlet and each channel outlet is provided with its own protective valve. Closing the channel inlet or outlet by a valve is typically driven by gravitational forces, and is intended to prevent water to splash into the housing via the channel inlet and channel outlet. In particular when the device is not in use, but is nonetheless in a moist environment, such as a shower, this may prevent moisture from entering into the housing. Preferably, each channel inlet is provided with at least one protective valve and each channel outlet is provided with at least one protective valve. Preferably, at least one valve comprises a flap which is hingeably mounted by the housing, and which is forced, when the fan is off and due to gravitational forces, towards a position wherein the flap substantially closes the channel inlet and/or channel outlet. Preferably, the at least one cooling channel inlet and the at least one cooling channel outlet are located in line, in particular side by side, in width direction of the housing. This specific orientation leads to a relatively efficient arrangement of channel inlet(s) and channel outlet(s), which allows the device to be encased in a wall of a humid room in a more pronounced manner, which allows the protruding part of the housing which is positioned in front of said wall to be as small as possible, which is favourable from a practical and aesthetical point of view. This latter can in particular be realized in case the at least one cooling channel inlet and the at least one cooling channel outlet are located in a front section of the bottom part of the housing. Preferably, the depth of said front section is preferably approximately 2 cm or less. This may also define the depth of the protruding part of the housing which protrudes with respect to the wall of a humid room. It may be favourable that the width of the front section of the housing is larger than the width of a rear section of the housing. This not only facilitates installation of the housing in a wall, but also allows a relatively wide design of the channel inlet(s) and channel outlet(s) which allows reduction of the required depth of these inlet(s) and outlet(s) to convey sufficient cooling air through the device, which is in favour of the mounting depth of the housing in said wall. Preferably, the device, in particular the cooling circuit, comprises a plurality of cooling channel outlets which mutually enclose at least one cooling channel inlet. Preferably, the channel inlet width is at least five times the channel inlet depth. Preferably, the channel outlet width is less than three times the channel outlet depth. Preferably, the channel inlet depth is identical to the channel outlet depth. This facilitates to realize a pressure build-up within the housing by means of the at least one fan. Preferably, an air separating element is applied which is accommodated within the housing, in particular a bottom segment of the housing in order to separate sucked up fresh air from already heated air to be released. It is imaginable that the air separating element makes integral part of the housing. The air separating element may also be configured as support structure for e.g. one or more fans, a securing element (see below), and/or one or more of the aforementioned valves.

In a preferred embodiment of the device, the device comprises a plurality of radiation units. The reflector(s) of said radiation units are preferably shared reflector(s), which means that each reflector may serve as reflector for a plurality of radiation sources. Preferably, the assembly of radiation units comprises a plurality of UV radiation sources and a plurality of IR radiation sources. Preferably, the radiation sources are oriented substantially aligned. Preferably, each IR radiation source faces at each terminal end at least one UV radiation source. Typically, each radiation source is mounted to at least one reflector by using mounting elements which are attached to said at least one reflector and which co-act with end sections of a radiation source.

In a preferred embodiment, each radiation unit comprises a rear reflector for mounting at least one radiation source by means of at least one mounting element, and at least one front reflector positioned in front of said rear reflector and connected to said rear reflector, wherein each radiation source is positioned in front of said front reflector, and wherein at least one front reflector preferably comprises at least one through-hole for allowing said at least one mounting element to pass said front reflector. Typically, the one or more IR radiation sources are mounted to the front reflector by means of mounting elements, and the one or more UV radiation sources are mounted on the rear reflector by means of (other) mounting elements. The mounting elements of the IR radiation sources could e.g. be formed by steel elements. The IR radiation source is typically a IR lamp with a preferred power of at least 900 W. The IR radiation source is also known as heat lamp. The mounting elements of the UV radiation sources could e.g. be formed ceramic elements each supported by a metal foot. The UV radiation source is typically a low-pressure or high-pressure gas discharge lamp, such as a high-pressure bulb with a typical power of 400 W. Typically these lamps are filled with mercury. The UV radiation source is also known as tanning lamp. The primary function of the front reflector is to reflect radiation towards the user. Typically this front reflector is at least partially made of a highly reflective material and/or a highly diffusive material, such as aluminum. This leads to a relatively high radiation output with a homogeneous and smooth radiation pattern. The front reflector is preferably curved. The rear reflector has a primary function to shield the housing from radiation, which could deteriorate and degrade the housing material, and hence the lifetime and reliability of the device as such. The rear reflector is typically made of galvanized steel, which is capable of absorbing of significant amount of heat (which reduces heat absorption by the housing and the wall), although other materials are also imaginable. The front reflector and the rear reflector preferably mutually enclose an air space which serves as thermal insulation space, which prevents the housing to be heated significantly. The rear reflector and the housing preferably also enclose an air space which serves as additional thermal insulation space. Typically, the rear reflector is mounted at its opposing lateral edges to the housing. The front reflector may entirely be supported by the rear reflector. Preferably, the front reflector and the rear reflector are mutually fixed. Preferably, the assembly of the rear reflector and front reflector is mounted hingeably within the housing. To this end, the reflector assembly is provided with a stationary reflector mounting frame or mounting strip which is fixedly attached to the housing, and wherein the reflector assembly is hingeably connected to said stationary mounting frame of mounting strip. Typically, this mounting frame or mounting strip is made of metal. This embodiment allows said assembly to be hinged between an operational state and a service state. In the operational state the device is operational is ready to radiate a user. In the service state, the device is not operational, and the (outer) wall will have to be removed in order to hinge the said reflector assembly to the service state. In the service state, a maintenance person will have access to a (service) space behind the reflector assembly, which (service) space is typically equipped with electronics, such as the main controller, the power supply, and other electronic components. Preferably, the reflector assembly is initially, before first maintenance, secured and fixed in the operational state, typically by means of one or more breakable connections between the reflector assembly and the stationary mounting frame or mounting strip. These one or more breakable connections serve(s) as tamper evident closure. Upon first maintenance the breakable connection(s) will be broken after which the reflector assembly can be hinged.

Preferably, the outer surface of the housing is a substantially smooth surface. A smooth surface will typically facilitate installation of the device and may improve the water barrier properties of the device, in particular in case the coupling profiles are hidden from the outside of the device. preferably, the outer surface of the housing is matt.

The device may comprise an outer watertight casing (outer container) configured to enclose the housing at least partially, wherein said casing is preferably configured to be encased in a wall of a humid room. This casing will further improve the waterproof properties of the device and provides additional protection against moisture that may be present behind the device. Typically, this casing is made out of a single piece of polymeric material. The casing may e.g. be formed by thermoforming and/or vacuum moulding.

The device according to the invention can be mounted onto a wall, in particular a wall of a humid room, in a corner defined by two of said walls, or the device can be partially encased by said wall. In an alternative embodiment, each support element defines a slot, wherein that the support frame comprises a plurality of protruding elements (in addition to slots or instead of slots) configured to be accommodated within said slots of the housing for mounting the radiation transmitting wall to the housing.

The invention further relates to a housing for use in a device according to the invention, wherein the housing comprises a circumferential wall and a rear wall connected to said circumferential wall, wherein said housing defines an accommodating space, and wherein opposing inner surfaces of the circumferential wall are provided with support elements for mounting a radiation transmitting wall.

The invention also relates to an assembly for use in a device according to the invention, said assembly comprising a radiation transmitting wall and a support frame, directly or indirectly, attached to a rear side of said wall, wherein said support frame comprises a plurality of slots configured to co-act with the support elements of the housing for mounting the radiation transmitting wall to a housing of the device.

The present invention will hereinafter be further elucidated based on the following non-limitative drawings, wherein.

Figure 4A:
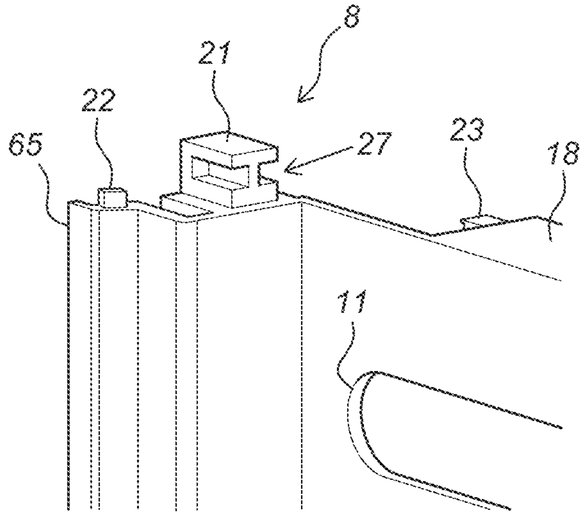
Figure 4B:
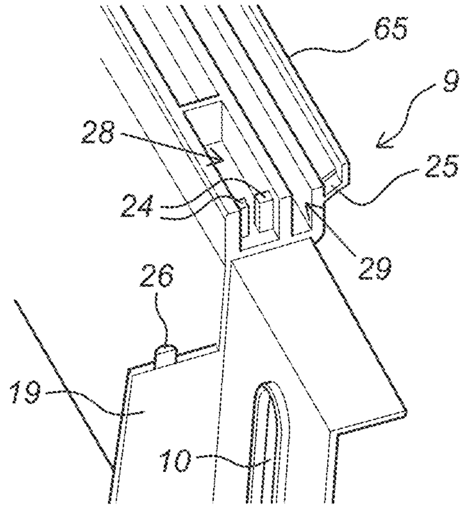
Figure 4C:
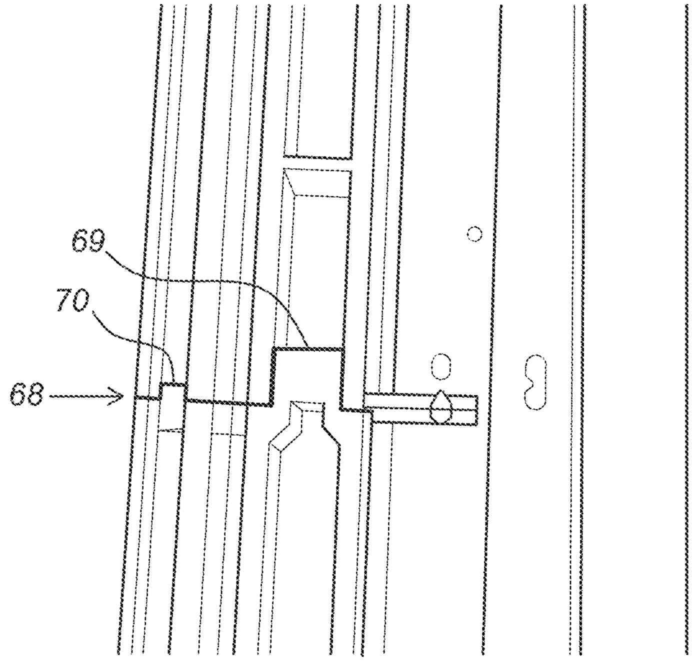
Figure 5:
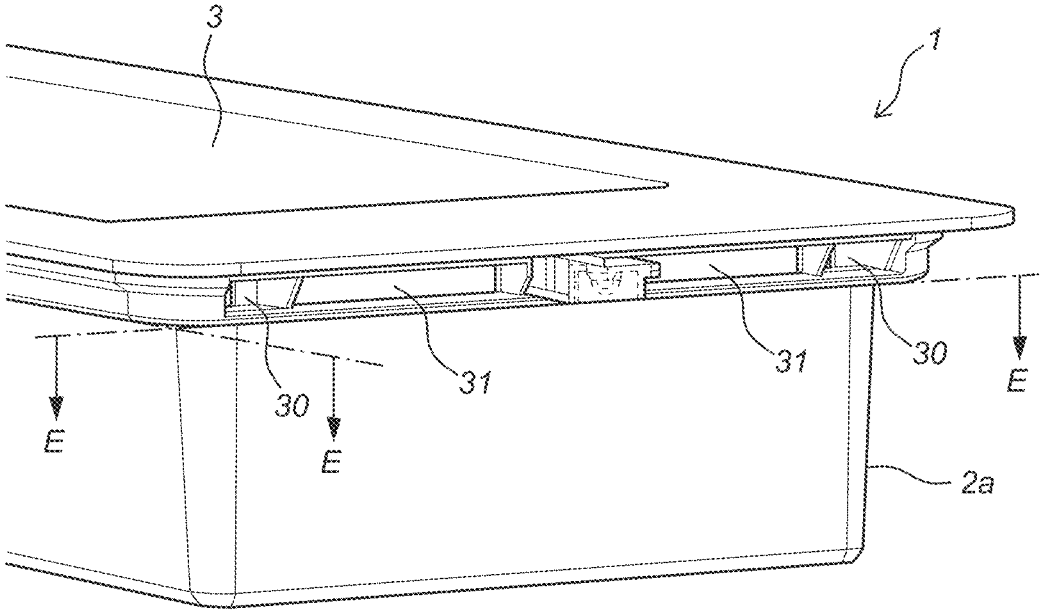
Figure 6:
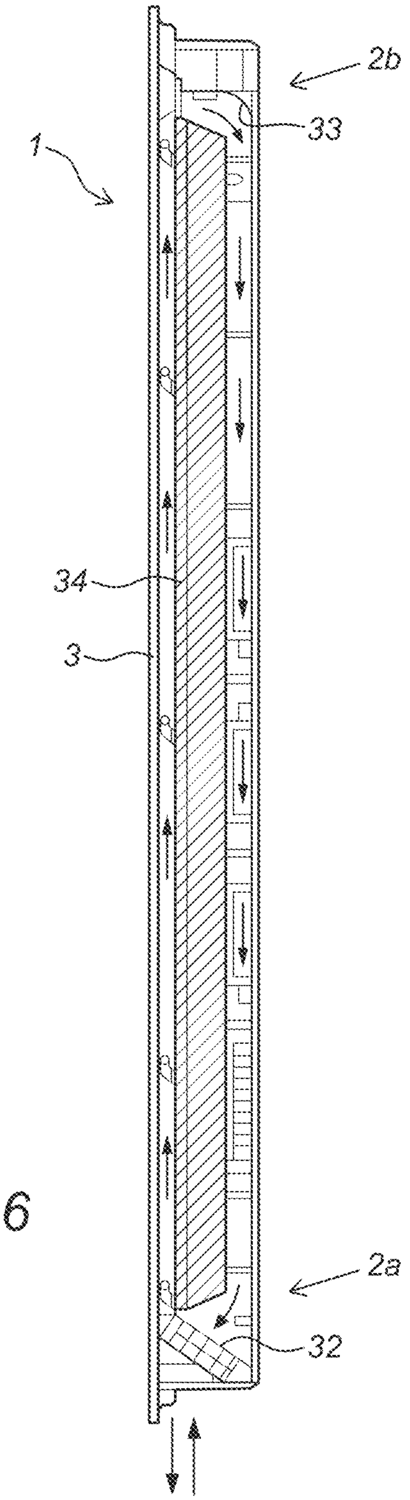
Figure 7A:
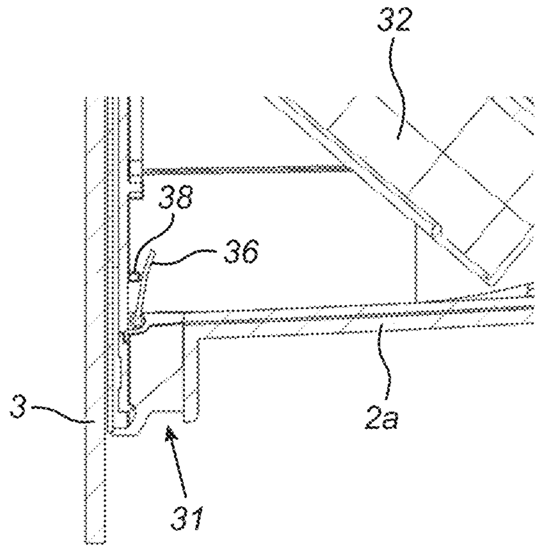
Figure 7B:
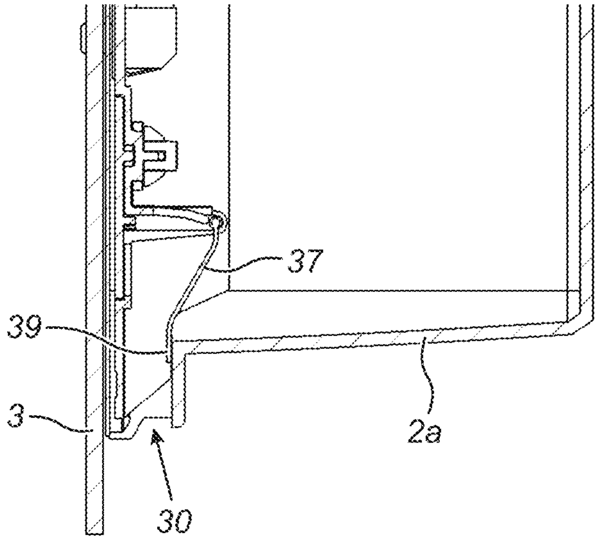
Figure 8:
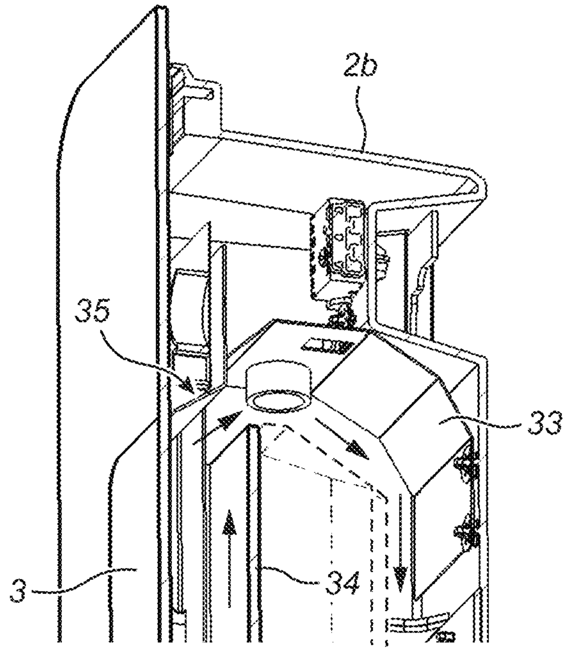
Figure 9:
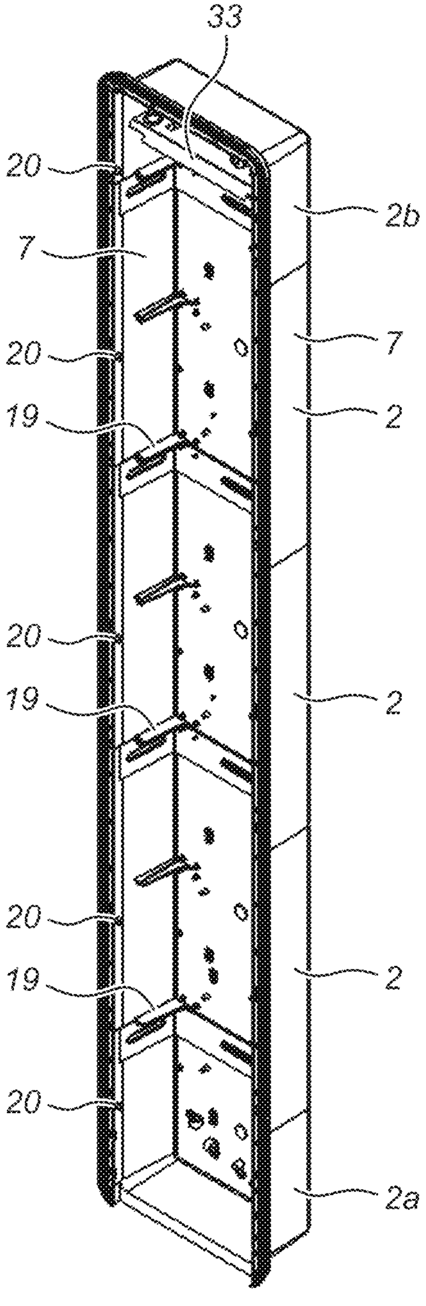
Figure 10A:
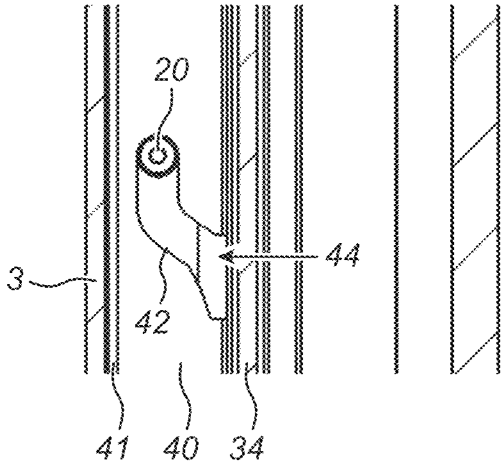
Figure 10B:
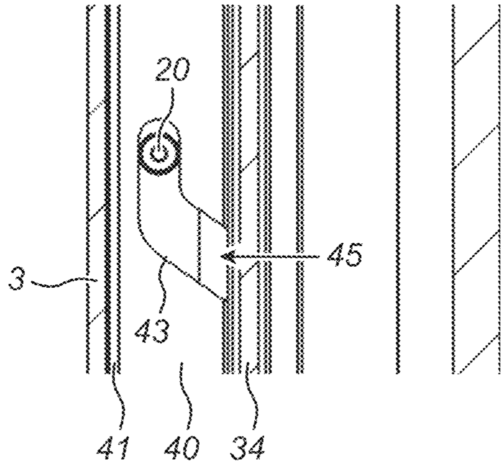
Figure 11:
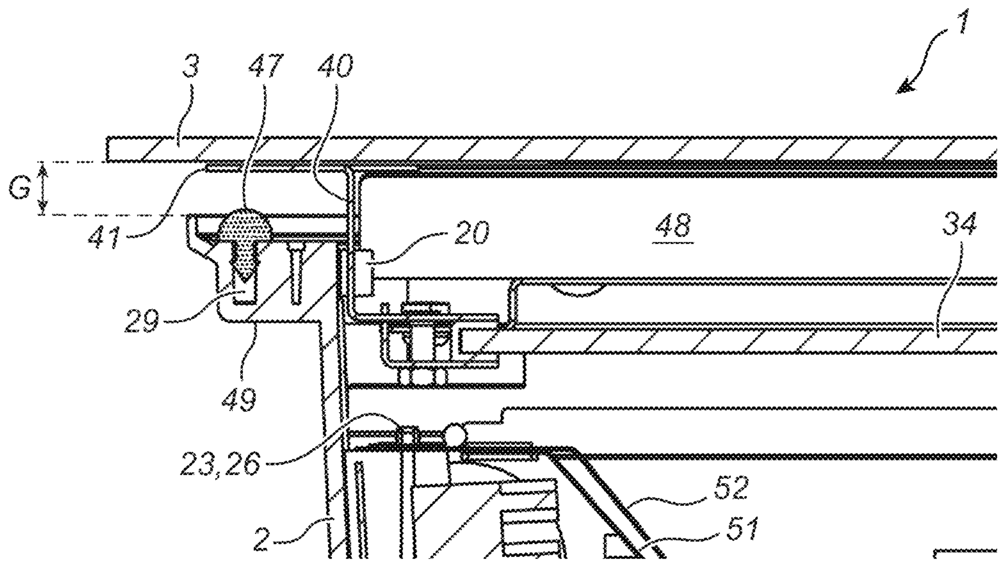
Figure 12:
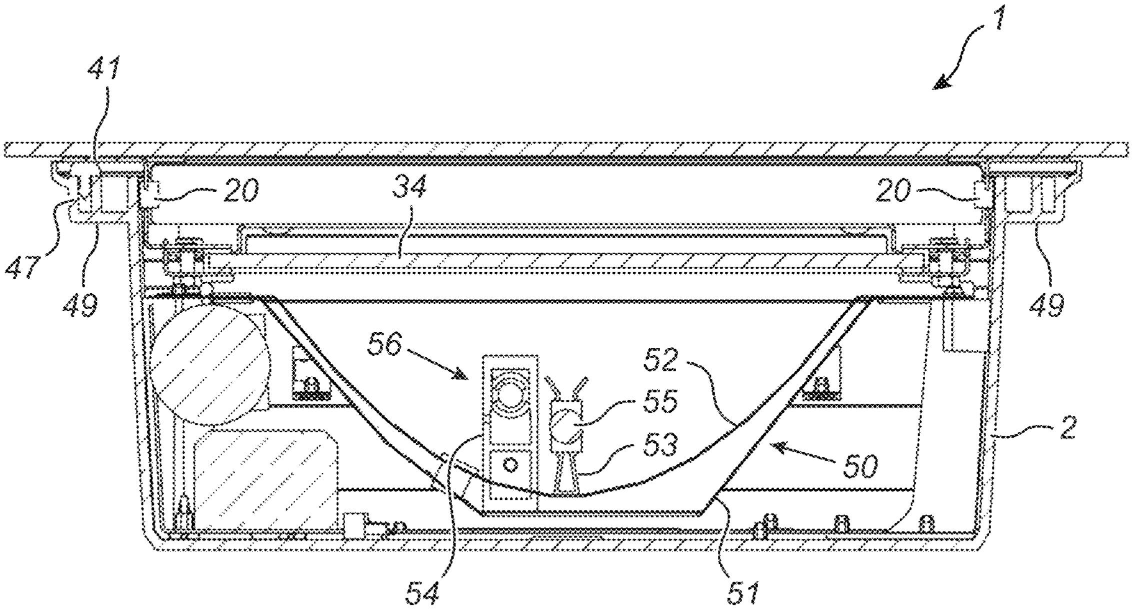
Figure 13:
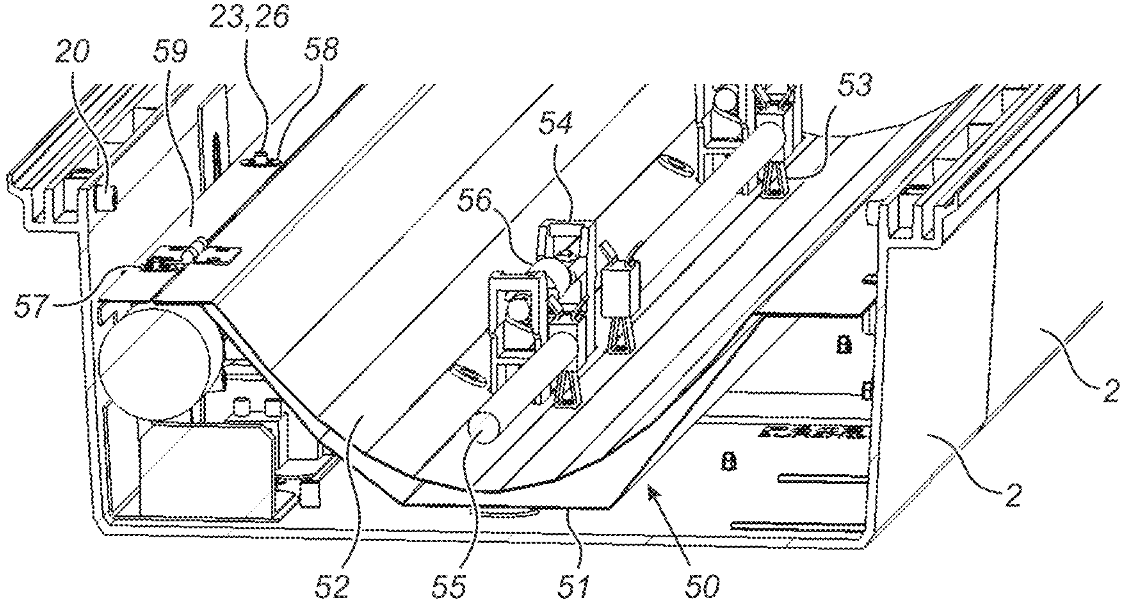
Figure 14A:
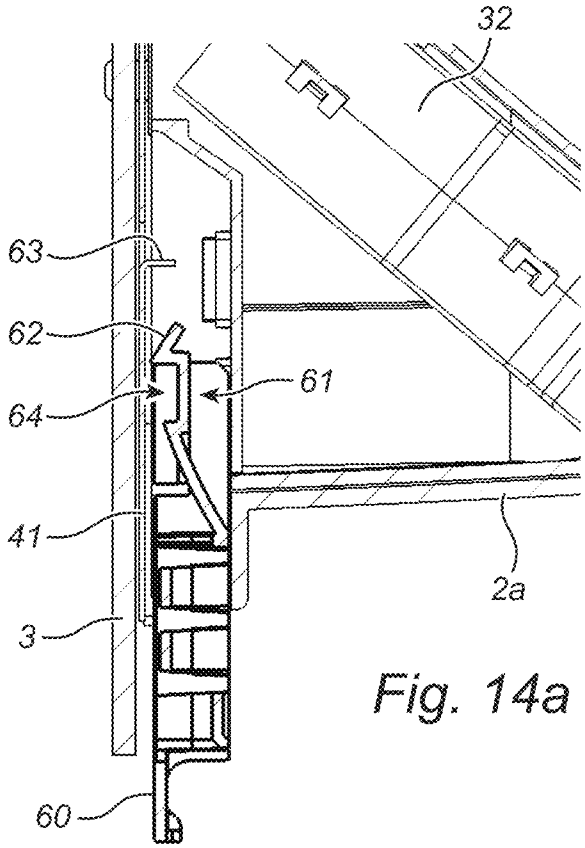
Figure 14B:
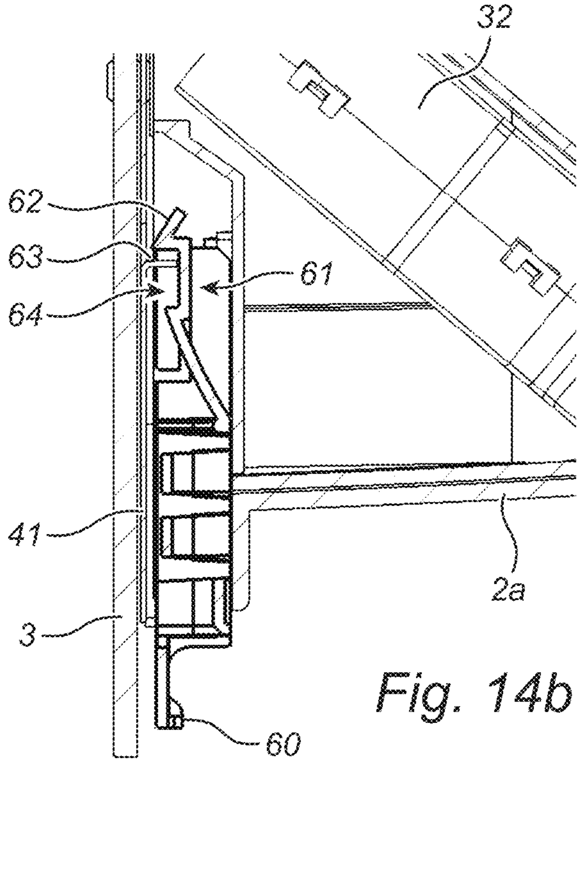

FIGS. 4*a* and 4*b* respectively show a pair of coupling elements of two housing segments;

FIG. 4*c* depicts the coupling elements of FIGS. 4*a* and 4*b* in coupled condition;

FIG. 5 depicts a bottom side of the device according to the invention;

FIG. 6 shows a cross section of the device;

FIGS. 7*a* and 7*b* show a cross section of the device along respectively an air inlet and an air outlet of the housing;

FIG. 8 shows a cross section of a top side of the device;

FIG. 9 depicts an opened up perspective view of the housing according to the invention;

FIGS. 10*a* and 10*b* show a part of a first locking slot and a second locking slot of a glass frame respectively;

FIG. 11 shows a cross section in width direction of a part of the device;

FIG. 12 shows a cross section in width direction of the device;

FIG. 13 shows a cross section of the housing and reflector system;

FIGS. 14*a* and 14*b* show a locking lip in an unlocked and in a locked position respectively; and FIGS. 15*a*-15*e* show the device in different installed conditions.

Figure 1:
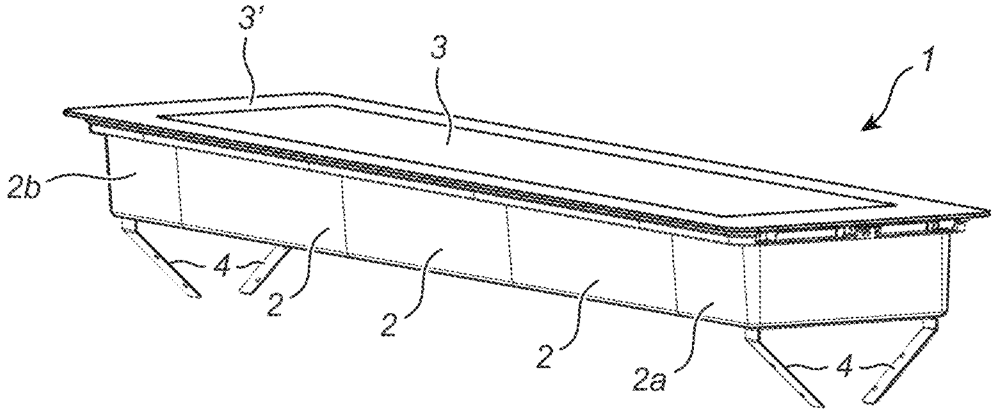
FIG. 1 shows a perspective view of the device according to an embodiment of the present invention.
Figure 2:
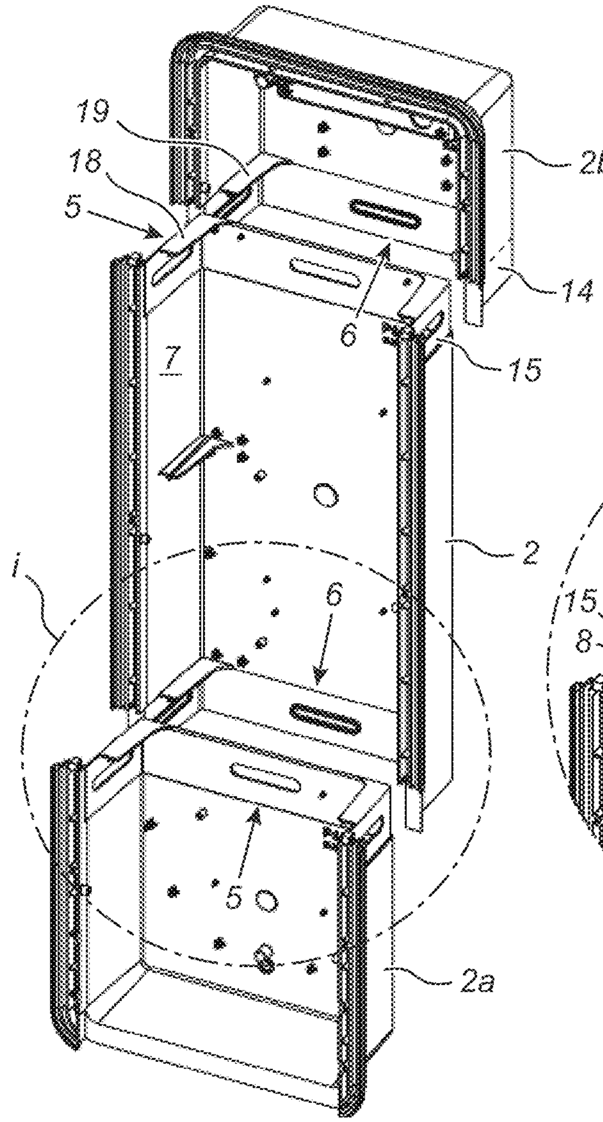
FIG. 2 shows an exploded perspective view of an embodiment of a housing of the device according to the invention.

FIG. 1 shows a perspective view of a device for radiating UV and/or IR radiation to a human body 1 according to a non-limitative embodiment of the present invention. Thereto, the device for radiating UV and/or IR radiation to a human body (1) is provided with a plurality of housing segments (2, 2*a*, 2*b*) which together form a lighting housing. The device for radiating UV and/or IR radiation to a human body at least comprises a bottom housing segment (2*a*), a top housing segment (2*b*), and at least one intermediate housing segment (2). In this exemplary embodiment the device for radiating UV and/or IR radiation to a human body (1) is provided with three intermediate housing segments (2), such as to form a larger device (1). That is, the number of intermediate housing segments (2) can be easily adjusted to increase or decrease the size of the device (1) in order to fit to a specific purpose or location. The embodiment depicted in FIG. 1 is provided with two sets of mounting brackets (4). This particular type of mounting bracket (4) is in particular suitable for mounting the device (1) in a corner where two walls meet. Although it is preferred to be a perpendicular corner between two walls, the invention is not limited thereto. The angle between the two mounting brackets (4) can be adjusted to suit the corner. It is also conceivable that the device (1) is connected to a wall, to this end the device (1) may be provided with an alternative mounting bracket (4). A, preferably transparent, outer glass sheet (3) may be provided on top of the device (1). Around the perimeter of said transparent outer glass sheet (3) there may be a border sheet (3'), which may be either formed out of glass, or another material. It is conceivable that if said border sheet (3') is composed out of glass, it may be integrally connected to the outer glass sheet (3), wherein by means of for example a material treatment, said border sheet (3') may have been given a different appearance. It is conceivable that said outer sheet and/or border sheet (3, 3') are provided with a glass frame or support frame. Said frame may be adhered by means of an adhesive or the like. Preferably, the sheets of glass (3, 3') extend beyond the perimeter of the frame for providing a more attractive appearance. Alternatively, the border sheet (3') may be integrally formed by a frame, and wherein said border sheet (3') serves as a surface for attaching the outer glass sheet (3) to. Said frame may be for example formed out of a plastic, or for example aluminum. On the flat surfaces of said frame, which as such form the border sheet (3') the outer glass sheet (3) may be adhered FIG. 2 shows an exploded perspective view of the housing of the device (1). In this figure the housing is embodied by a bottom housing segment (2*a*), a top housing segment (2*b*), and one intermediate housing segment (2) provided between said bottom and top housing segments (2*a*, 2*b*). Each of the top and bottom housing segments (2*a*, 2*b*) comprise a side wall (7) which extends along at least three sides of said housing segment (2*a*, 2*b*), the intermediate housing segment (2) may comprise at least two side walls (7) extending along two opposing edges of the intermediate housing segment (2). On top of the side wall (7) a housing edge may be provided, which may extend along at least one of the side walls (7) of each housing segment (2, 2*a*, 2*b*). The housing segments (2, 2*a*, 2*b*) are configured to be mutually connected to each other. In order to connect the housing segments (2, 2*a*, 2*b*) to each other, the housing segments (2, 2*a*, 2*b*) are provided with first coupling edge (5) and a second coupling edge (6). The first and or second coupling edges (5, 6) may also be referred to as coupling profiles (5, 6). In particular each bottom housing segment (2*a*) comprises at least a first coupling edge (5), and each intermediate housing segment (2) comprises bot a first and second coupling edge (5, 6), and the top housing segment comprises at least a second coupling edge (6). The first coupling edges (5) are configured for coupling with a second coupling edge (6) of an adjacent housing segment (2, 2*a*, 2*b*). Since the device (1) according to the invention is in particular suitable for use in humid or wet environments, such as a shower, the device (1) should be able to prevent water from entering the system. To this end, the housing segments (2, 2*a*, 2*b*) are at least partially overlapping, it is conceivable that said overlapping portions form part of the coupling edges (5, 6). As shown in FIG. 2, the top housing segment (2*b*) comprises a side wall portion (14), wherein an interior side of the side wall portion (14) will in installed condition abut against the exterior side of the side wall portion (15) of the intermediate housing segment (2) the top housing segment (2*b*) is connected to. Hence the side wall portions (14, 15) overlap when the top housing segment (2*b*) is connected to the intermediate housing segment (2). This overlap may prevent water from seeping in through a gap. In order to align two housing segments (2, 2*a*, 2*b*) the housing segments are provided with guide elements (18, 19), which may additionally serve as an extra lock between two housing segments (2, 2*a*, 2*b*), which will be elaborated with reference to FIGS. 4*a* and 4*b*. The circle depicted with reference (i) is shown in FIG. 3 in more detail, with reference to which figure the respective first and second coupling edges (5, 6) will be elaborated in more detail.

Figure 3:
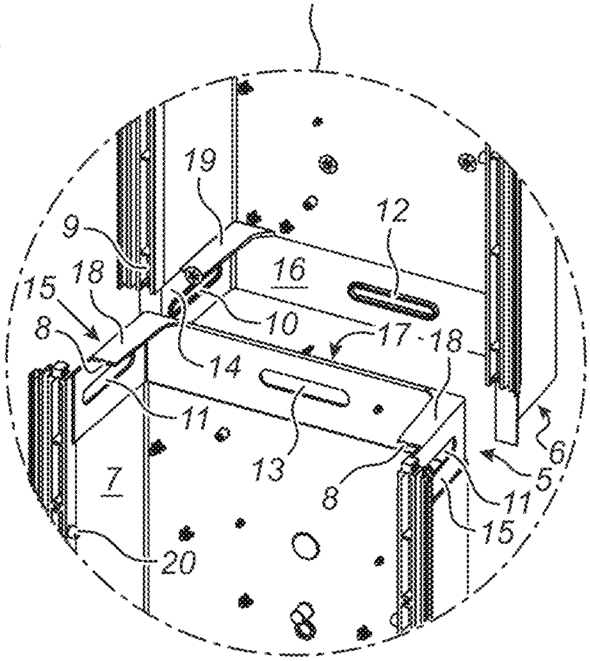
FIG. 3 shows an enlarged portion of the housing as shown in FIG. 2.

FIG. 3 shows an enlarged perspective view of the bottom housing segment (2*a*) and the intermediate housing segments (2) as shown in FIG. 2. The first coupling edge (5) comprises two edge locking elements (8), said two edge locking elements (8) configured for releasably lockingly co-acting with two edge locking slots (9), or complementary counterlocking elements (9), of an adjacent second coupling edge (6). Further, the first locking edge (5) is provided with three locking recesses (11, 13), wherein two locking recesses (11) are provided in a part of the side wall (7) of a housing segment (2, 2*a*, 2*b*), and one locking recess (13) is provided in a bottom surface of a housing segment (2, 2*a*, 2*b*). Said locking recesses (11, 13) of the first coupling edge (5) are configured for releasably lockingly co-acting with three locking protrusions (10, 12) of an adjacent second coupling edge (6). Two locking protrusions (10) are provided in a part of the side wall (7) of a housing segment (2, 2*a*, 2*b*) such as to co act with the two locking recesses (11) that are in a part of the side wall (7) of an adjacent housing segment (2, 2*a*, 2*b*). Similarly, the locking protrusion (12) provided in the bottom surface of the housing segment (2, 2*a*, 2*b*) is configured to co-act with the locking recess (13) provided in the bottom surface of an adjacent housing segment (2, 2*a*, 2*b*).

In a coupled condition of the two housing segments (2, 2*a*, 2*b*) the two locking recesses (11) provided in a part of the side wall (7) of the housing, together with the locking protrusions provided in a part of the side wall (7) of an adjacent housing segment (2, 2*a*, 2*b*) are configured for restricting a movement of two coupled housing segments that is situated in the plane of the side wall (7). Similarly, the locking protrusion (12) provided in the bottom surface, together with the locking recess of an adjacent housing segment (2, 2*a*, 2*b*) are configured for restricting a movement of two coupled housing segments (2, 2*a*, 2*b*) that is situated in the plane of the bottom surface. Complementary to the locking recesses (11, 13) and the locking protrusions (10, 12), two adjacent housing segments (2, 2*a*, 2*b*) are further mutually locked through two edge locking elements (8) provided on an end portion of a part of the rim of a housing segment (2, 2*a*, 2*b*), said two edge locking elements (8) are configured for releasably lockingly co-acting with two edge locking slots (9) which are situated on an end portion of a part of the rim of an adjacent housing segment (2, 2*a*, 2*b*). Said edge locking elements (8) and edge locking slots (9) at least partially prevent the two locked housing segments (2, 2*a*, 2*b*) to move in a direction parallel to the rim. Further to the aforementioned, two co-acting guide elements (18, 19) are provided, one on each of the first or second coupling edge (5, 6). In coupled condition of two adjacent housing segments (2, 2*a*, 2*b*) said co-acting guide elements (18, 19) abut against one another, whereas during the coupling, the two co-acting guide elements (18, 19) may be used to slide over one another, such as to facilitate a proper coupling. All of the mentioned elements that are used four coupling two adjacent housing segments (2, 2*a*, 2*b*) may be beneficial to the waterproofing of the housing. To this end, at least one of the locking recesses (11, 13) or locking protrusions (10, 12) may further be provided with a sealing member. Such a sealing member may for example be a rubber ring, which is fitted in or around the at least one of the locking recesses (11, 13) or locking protrusions (10, 12) such as to further prevent water from flowing therethrough. Preferably, at least one housing segment (2, 2*a*, 2*b*) is provided with a support element (20), which is configured for guiding a (part of a) frame.

FIGS. 4*a* and 4*b* show a portion of the first and second coupling edge (5, 6) respectively, in particular the edge locking element (8) and the edge locking slot (9) of two respective housing segments (2, 2*a*, 2*b*). The edge locking element (8) may be in the form of a block (21), which may comprise two recessed slots (27), said slots (27) each at least partially extending over a part of two opposing side surfaces of the block (21), and both extending to at least one end surface of the block (21) both opposing surfaces are connected to. As such an "H" shaped bottom side is formed as depicted in FIG. 4*a*. At a distance from the block (21) there may be a second edge locking element (22) in the form of a protrusion (22). Additionally or alternatively, a third edge locking element (23) may be provided on the first coupling edge (5). Said third edge locking element (23) may be provided on one of the guide elements (18). FIG. 4*b* depicts the edge locking slot (9) of the second coupling edge (6). On an upper side of the edge, an edge recess (28) is provided, in which edge recess (28) two retaining protrusions (24) are situated. Said retaining protrusions are situated at opposing sides of the edge recess (28). The aforementioned recessed slots (27) provided in the block (21) are configured to co-act with the retaining protrusions (24) of the edge recess (28) of an adjacent housing segment (2, 2*a*, 2*b*). At a distance from the edge recess (28) a cut-out notch (25) is provided. Said cut-out notch (25) is configured to receive a second edge locking element (22) of an adjacent housing segment (2, 2*a*, 2*b*). Further a fourth locking element (26) is provided on a second coupling edge (6), in particular on a guiding element (19) of the second coupling edge (6). Said fourth edge locking element (26) is configured to co-act with a third edge locking element (23) of an adjacent housing segment (2, 2*a*, 2*b*). Said third and fourth edge locking elements (23, 26) may in an coupled condition of two adjacent housing segments (2, 2*a*, 2*b*) be coupled through a retaining ring. The cut-out notch (25) and the edge recess (28) of the second coupling edge (6) are mutually separated by a channel (29). Said channel (29) may extend along the entire edge of a housing segment (2, 2*a*, 2*b*). Further, the edge of at least a part of the housing segments (2, 2*a*, 2*b*) may comprise an outer upward portion (65), which portion may define a part of an insertion space for a part of the outer glass sheet (3) or the outer glass sheet frame (40, 41), in particular for the parallel frame portion (41). Said parallel frame portion (41) may in fully installed position of the outer glass sheet (3) be substantially flush with the outer upward portion (65) of the edge. In FIG. 4*c*, a part of the first and second coupling profile (5, 6) are depicted in a coupled condition. In particular the edge locking element (8) and the edge locking slot (9) of two respective housing segments (2, 2*a*, 2*b*) are in coupled condition. As such, a seam (68) is formed between the two housing segments (2, 2*a*, 2*b*). The seam (68), seen from a top view, has a substantially non-linear shape. In this particular embodiment the seam is block-shaped. In order to prevent water from penetrating into the housing from the outside, which would typically be on the left side as depicted in the figure, a central part, or a inner seam section (69) is located higher with respect to an outer section (70) of the seam.

FIG. 5 depicts another aspect of the device (1) according to the present invention. This aspect is related to the ventilation of the device (1). In the bottom housing segment (2*a*) a plurality of venting holes (30, 31) may be provided. In this non limitative embodiment, two air inlet vents (31) are provided, and two air outlet vents (30) are provided. The air vents (30, 31) serve to cool the device (1) according to the present invention. Besides cooling electronic components housed inside the housing segments (2, 2*a*, 2*b*), air is also used to cool down the outer sheet of glass (3) and/or the border sheet (3') such that the temperature of these features does not exceed a predetermined temperature. Through the two inlets (31) cool air is sucked into the device (1). The cool air passes through the device (1) as it heats up due to heat shed by the components inside. The hot air is forced out of the device (1) through the air outlets (30). The air vents (30, 31) are located on the bottom housing segment (2*a*) such as to prevent water from seeping into the device (1). If the device (1) is installed in a recess provided in a wall, it should be understood that the air vents (30, 31) should be in contact with cool air to prevent blockage of the vents (30, 31). To this end, FIG. 6 provides a view of the circulation of air through the device (1) according to the invention. A fan (32) is used to provide for a circulation of air. However, different means for causing cool air to enter the device (1), heat up inside, and leave through an air outlet (30) may be also suitable to this end. The ventilator may suck in cool air from the surrounding, through the air inlet (31), which cool air may be forced between the outer glass sheet (3) and an inner glass sheet (34), as indicated by the arrows in the figure. The outer glass sheet (3) and inner glass sheet (34) may otherwise be referred to as an inner and outer radiation transmitting cover element. Once the air has travelled towards the top housing segment (2*b*) the air is bended 180 degrees back towards the bottom housing segment (2*a*). This may be realized by means of a deflector plate (33), which will be elaborated in more detail later on. The air will flow back down below the reflector and leaves the interior of the device (1) through the air outlet (30) in the bottom housing segment (2*a*). Optionally, the housing (2, 2*a*, 2*b*) may be embedded in a shower wall, such that the device (1) is not so obtrusive and consumes less space. To this end, a back portion, starting from a line depicted in the figure in the direction indicated by the arrow (E), may in particular be embedded or built into a wall. This allows the air inlet (31) and air outlet (30) to still suck in and expel air from and into the surrounding, such that airways are not blocked. As shown clearly in this figure, the air inlets (31) and air outlets (30) are arranged in a side by side orientation of the device. As such, a more flush built-in of the device (1) is possible.

FIGS. 7*a* and 7*b* respectively show a cross section of the air inlet (31) and air outlet (30) in the bottom housing segment (2*a*). In FIG. 7*a* the air inlet vent (31) is shown in more detail. The air inlet (31) is provided with an inlet valve (36). In inactive condition, said air inlet valve (36) will be substantially horizontally due to its gravity. The inactive condition is considered as the condition wherein the fan (32) is not in operation. In this position the valve (36) may close off the air inlet vent (31) substantially entirely, such that in the case no flow of air is required through the system and hence the fan (32) is not turned on, the chances of moisture and/or water getting inside the system are further reduced since the air inlet vent (31) is blocked by the inlet valve (36). If the fan (32) is turned on the valve (36) will be in the position as shown in the figure. The position of the valve (36) is not entirely vertical in order to make sure the inlet valve (36) will block the air inlet vent (30) when the system goes into the inactive condition, that is, when the fan (32) is turned off. To ensure the valve (36) does not unintentionally end up in a vertical position a blocking element (38) is provided. The valve (36) may be hingeable connected to either the bottom housing segment (2*a*), or to a separate frame, or to a frame of the outer glass sheet (3). Similarly, the air outlet vent (30) also comprises a hingeable outlet valve (37) which prevents moisture and/or water from getting into the system in its inactive condition. The outlet valve (37) in FIG. 7*b* is depicted in a position which would occur when the system is in inactive condition, and hence the fan (32) is not on. As shown, the valve (37) essentially entirely closes the air outlet vent (30) such that no water can come inside. In order to prevent that the valve (37) remains stuck in an unintended position, and always goes back to the position as depicted when the system is in inactive condition, an extended valve portion (39) is provided. Said extended valve portion (39) abuts the outer glass sheet (3) or a part of the housing if the fan is active and as such prevent the valve (37) from rotating too far. As such, this will allow the valve (37) to essentially always revert back to the position as depicted in the figure when the system is in inactive condition.

FIG. 8 shows a cross section of the top housing segment (2*b*). FIG. 8 shows a more detailed view of the deflector plate (33) according to the invention. Said deflector plate (33) functions to deflect the upwardly travelling stream of air towards a downwardly travelling stream of air. Herein, the stream of air is depicted by means of the arrows. The upwardly travelling stream of air flows between the outer sheet of glass (3) and the inner sheet of glass (34). In addition to the deflector plate (33) a deflector bracket (35) may be provided. Said deflector bracket (35) serves as a first element for rearranging the upwardly travelling stream of air. In particular the deflector bracket (35) may introduce a tangential component to the stream of air. Said tangential component is to be understood as at least partially perpendicular to the upwardly travelling stream of air.

FIG. 9 shows a perspective view of the housing comprising a bottom housing segment (2*a*), a plurality of intermediate housing segments (2) and an upper housing segment (2*b*). Each housing segment (2, 2*a*, 2*b*) comprises at least one support element (20). The support elements (20) are in particular configured for guiding a frame, in particular the frame that is attached to the outer sheet of glass (3). Preferably each housing segment (2, 2*a*, 2*b*) comprises at least two support elements (20, which are allocated on opposing sides of a side wall (7) of the housing segments (2, 2*a*, 2*b*). This figure also illustrates how the plurality of housing segments (2, 2*a*, 2*b*) mutually form the accommodating space (72) of the device. By changing the amount of housing segments (2, 2*a*, 2*b*) that is used, the size of the accommodating space (72) may be chosen according to the size of the device. FIGS. 10*a* and 10*b* show a schematical view of a part of the frame (40, 41) the outer sheet of glass (3) may be attached to. The frame (40, 41) comprises a parallel frame portion (41) that is substantially parallel to the outer sheet of glass (3), and a perpendicular frame portion (40) that extends substantially perpendicular to the parallel frame portion (41). Hence, the perpendicular frame portion (40) therewith extends substantially perpendicular to the outer sheet of glass (3). Said perpendicular frame portion (40) may be provided with a first locking slot (42) and a second locking slot (43). The first and second locking slot (42, 43) are configured for sliding over the support elements (20). It is conceivable that the perpendicular frame portion (42) is provided with a plurality of first and/or second locking slots (42, 43). Preferably, the first and second locking sots (42, 43) are provided at opposing sides of the perpendicular frame portion (40), such that the first and second locking slots (43, 44) are configured to co-act with the support elements (20) of the housing segments (2, 2*a*, 2*b*). The first and second locking slots (43, 44) may have mutually different intake openings (44, 45) and slightly different slot trajectories. This is especially beneficial to prevent the attaching mechanism to be overdetermined. To this end, one pair of opposing first locking slots (42) provided with first intake openings (44) may be arranged in the housing, preferably at a central part of the housing. Additionally, a plurality of pairs of second locking slots (43) with second intake openings (45) may be arranged in the housing. The first and second intake openings (44, 45) may be positioned above the plurality of support elements (20), once the openings (44, 45) are slid over the support elements (20), the first and second locking slots (42, 43) will determine the trajectory of the frame (40, 41) and therewith the outer glass sheet (3). The locking protrusions (20) will have a final position in the vertical portion of the first and second locking slots (42, 43).

FIG. 11 shows a cross section of a part of a housing segment (2). In this figure the outer glass sheet (3) is partially installed. This can be seen by the gap (G) present between the parallel frame portion (41) and the upper side of the housing edge (49). In this condition, the perpendicular frame portion (40), in particular the first and second locking slots (42, 43) provided and/or the first and second intake openings (44, 45) provided therein, have only partially received a support element (20), and thus said support elements (20) have not yet reached the vertical portion of the first and second locking slots (42, 43). The figure further shows the presence of a seal member (47), which may be embodied by a PTFE coated rubber or silicon. Said sealing member (47) may ensure a proper sealing between the housing segment (2) and the outer sheet of glass (3) and/or glass frame (40, 41). The sealing member (47) may be removably allocated in the edge channel (29), which edge channel (29) is provided in the housing edge (49). Additionally, the figure shows the space (48) between the outer glass sheet (3) and the inner glass sheet (34), through which space (48) the stream of air flows. After the support elements (20) have reached their locking position in the first and second locking slots (42, 42), that is, wherein the support elements (20) are in the vertical portion of said first and second locking slots (42, 43), the outer glass sheet will be in the position as depicted in FIG. 12.

FIG. 12 thus shows the outer sheet of glass (3) in its final position. As can be seen, the parallel frame portion (41) is pressing against the sealing member (47) such that the sealing member (47) prevents water from entering the housing segment (2). The double reflector (50) is also shown in FIG. 12. Said double reflector (50) comprises an inner reflector member (52) and an outer reflector member (51). The inner reflector member (52) has a segmented parabolic shape, such that light from either the ultraviolet (UV) lamp (56) or the infrared (IR) lamp (55) is reflected towards the inner glass sheet (34) and the outer glass sheet (3). Said UV lamp (56) is attached to the outer reflector member (51) and is attached to said outer reflector member (51) with a UV lamp frame (54) which extends through a hole provided in the inner reflector member (52). The IR lamp (55) is attached to the inner reflector member (52) through a IR lamp frame (53). FIG. 13 provides a perspective view of a part of the cross section as shown in FIG. 12. The UV lamp (56) is clearly visible in FIG. 13. Said UV lamp (56) is suspended in two UV lamp frames (54) which, as shown in FIG. 12, extend through the inner reflector member (52). The double reflector (50) is in this non-limitative embodiment attached to the housing via a hinge (57). The hinge (57) allows the entire double reflector (50) to be upwardly hinged, such that any electronic component housed below the double reflector (50) may be more accessible. The hinge (57) may connect to the double reflector (50) on one side, and to an attachment plate (59) on the other side. The attachment plate (59) may be directly or indirectly connected to the housing. It is conceivable that said attachment plate (59) is provided with at least one hole (58). Said hole (58) may be configured to co-act with the mutually adjoined third edge locking element (23) and fourth locking element (26), such that the third and fourth (23, 26) locking element essentially define a location for placing the attachment plate (59).

Lastly, FIGS. 14*a* and 14*b* depict a cross section of the bottom housing segment (2*a*) wherein the outer glass sheet (3) and glass frame (40, 41) is depicted in two different positions. FIG. 14*a* depicts the bottom housing segment (2*a*) wherein the outer glass sheet (3) and the frame attached thereto (40, 41) is not yet in its final position. In this, not fully installed, position an indicator element (60) is visible from the outside of the device (1). The indicator element (60) may otherwise be referred to as a securing element (60). Said indicator element (60) may serve to warn a user that the outer glass sheet (3) and the frame (40, 41) are not yet fully installed. The indicator element (60) makes the user aware of the fact that the outer glass sheet (30) is not yet locked. That is, the outer glass sheet (3) may still be upwardly lifted and removed from the housing. The user, or the person installing the device (1) should push the indicator element (60) upwardly in order to lock the outer glass sheet (3). In other to achieve this lock, a glass locking element (61) that may be directly attached to the indicator element (60) is configured to lockingly engage with a locking protrusion (63) of the outer glass sheet (3) or the parallel frame portion (41). An inclined portion (62) of the locking element (61) will slide over the locking protrusion (63) of the outer glass sheet (3). Once the inclined portion slid over the locking protrusion (63) the receiving recess (64) provided in the locking element (61) will prevent the outer glass sheet (3) from being moved upwardly since the locking protrusion (63) is trapped inside the receiving recess (64). As such, also the indicator element (61) is not visible anymore as shown in FIG. 14*b*. This informs the user or installer that the outer glass sheet (3) is locked properly. If it is needed to remove the outer glass sheet (3) in case of maintenance, a tool may be utilized to unlock the locking element (61). This may be realized by inserting from below said tool, such that the locking element (61) is bent slightly into a position wherein the locking protrusion (63) may be removed from the receiving recess (64). The tool may for example be a screw driver, or the like.

Figure 15A:
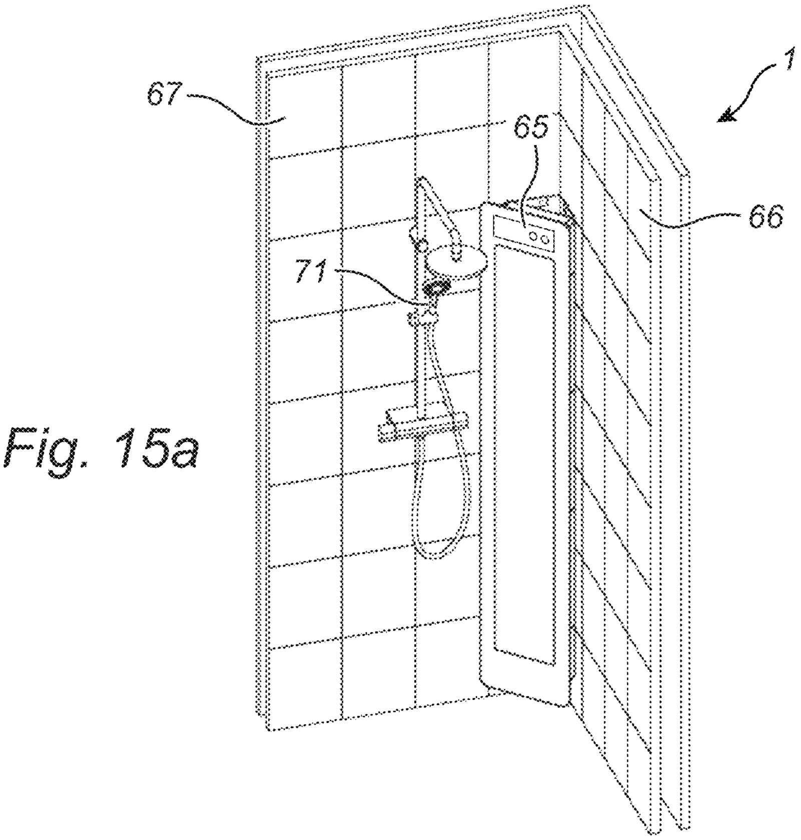
Figure 15B:
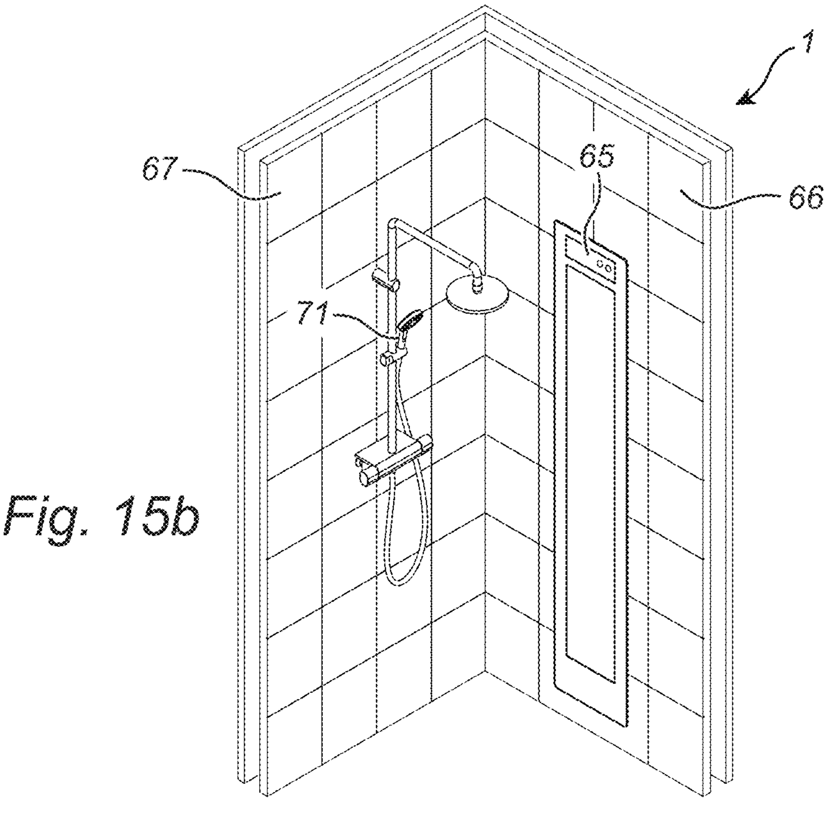
Figure 15C:
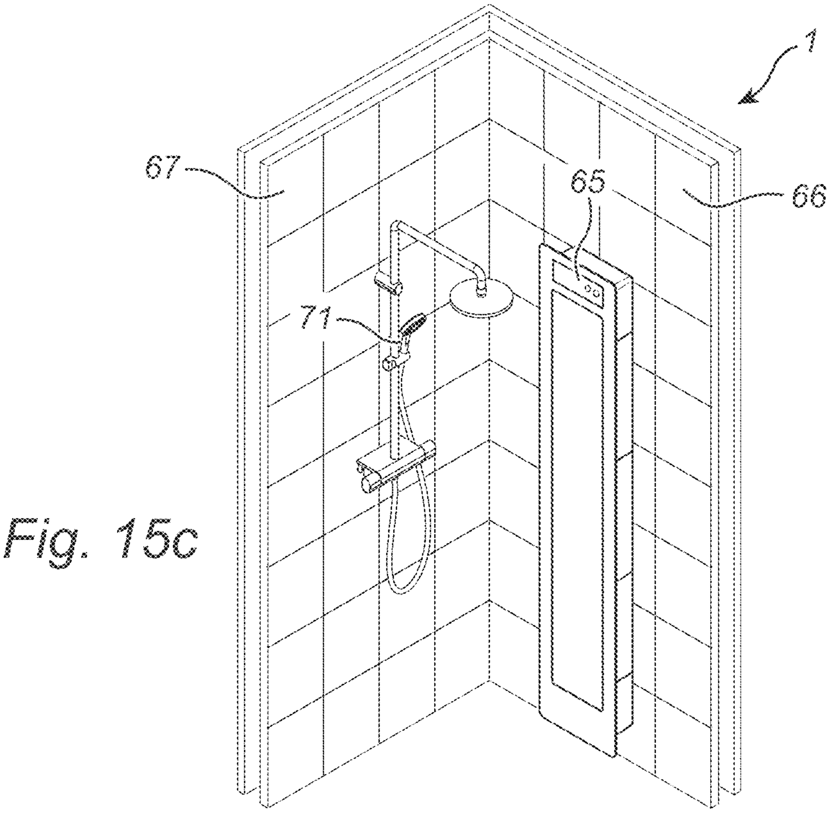
Figure 15D:
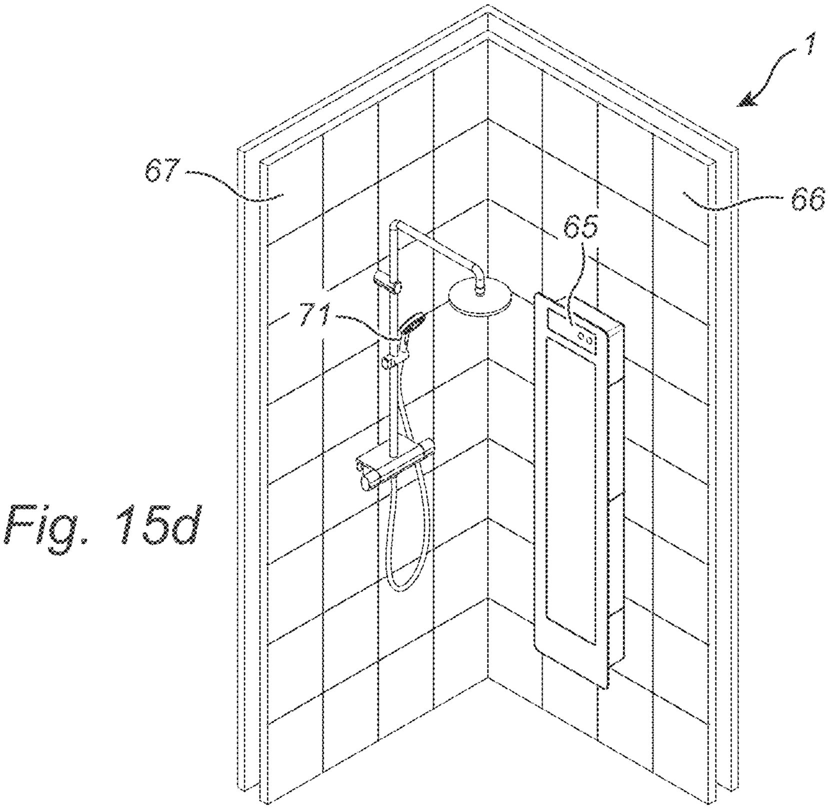
Figure 15E:
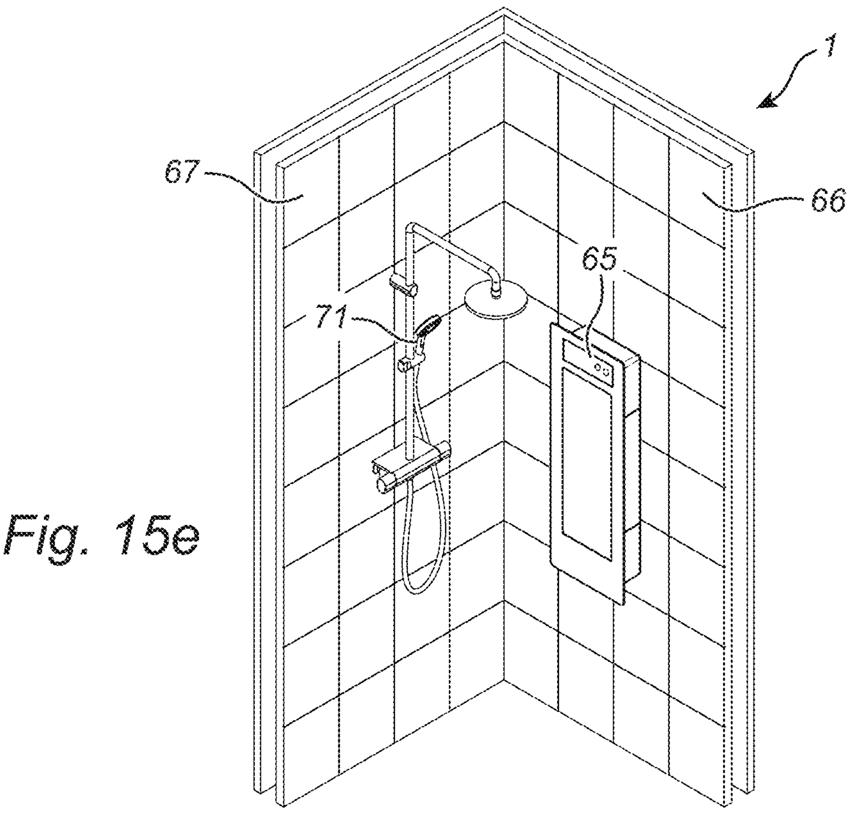

FIG. 15*a* is a first representation of the device (1) which is built into bathroom, in a shower for example. The device (65) may be operated by a user via an interface (65) which allows the user to select various modes of the device. The device (1) may as such be attached to either of the walls (66, 67), such as is depicted in FIGS. 15*b* and 15*c*, or may be attached in the corner enclosed by said walls (66, 67), such as shown in FIG. 15*a*. In FIG. 15*b* the device (1) is built into one of the walls (67), wherein the device emits UV or IR light into a direction of a user standing under the showerhead (71). The device (1) only slightly protrudes from the wall (67) it is built into, this is to prevent the air inlet and air outlet at the bottom side of the device (1) from blocking. As such, the device (1) is able to suck in air and also to expel air back into the environment through its in- and outlets. Due to a side by side orientation of the air inlet and outlet at the bottom side of the device (1) said device (1) may be built into the wall more deeply as compared to the prior art. FIG. 15*c* shows the same device (a) but attached onto the wall, instead of begin provided in a recess of the wall. Although in all of the FIGS. 15*a*-15*c* the same size device (1) is shown, the invention is not limited thereto, and also different sizes of the device (1) according to the invention may be installed similarly. The device (1) attached to one of the side walls (66) is shown in a first smaller sized embodiment in FIG. 15*d*, and in an even smaller sized embodiment in FIG. 15*e*. These smaller embodiments may however achieve the same benefits. The different sizes may in particular be realized by implementing respectively three, two, or just one intermediate housing segment 2 to form the housing.

The above-described inventive concepts are illustrated by several illustrative embodiments. It is conceivable that individual inventive concepts may be applied without, in so doing, also applying other details of the described example. It is not necessary to elaborate on examples of all conceivable combinations of the above-described inventive concepts, as a person skilled in the art will understand numerous inventive concepts can be (re) combined in order to arrive at a specific application.

By “complementary” coupling profiles is meant that these coupling profiles can cooperate with each other. However, to this end, the complementary coupling profiles do not necessarily have to have complementary forms. By locking in “vertical direction” is meant locking in a direction parallel to or coinciding with a plane defined by the device. By locking in “horizontal direction” is meant locking in a direction perpendicular to said plane defined by the device.

It will be apparent that the invention is not limited to the working examples shown and described herein, but that numerous variants are possible within the scope of the attached claims that will be obvious to a person skilled in the art.

The verb "comprise" and conjugations thereof used in this patent publication are understood to mean not only "comprise", but are also understood to mean the phrases "contain", "substantially consist of", "formed by" and conjugations thereof.

The invention claimed is:

1. Device for radiating UV and/or IR radiation to a human body, comprising:

an upright housing comprising a circumferential wall and a rear wall connected to said circumferential wall, wherein said upright housing defines an accommodating space;

at least one radiation unit accommodated within said accommodating space, wherein each radiation unit comprises at least one radiation source for radiating UV and/or IR radiation, and at least one reflector; and at least one radiation transmitting wall to close the accommodating space at least partially, wherein opposing vertical inner surfaces of the circumferential wall are provided with support elements, and wherein said radiation transmitting wall is provided with a support frame, directly or indirectly attached to a rear side of said radiation transmitting wall, wherein opposing vertical parts of said support frame comprises a plurality of slots configured to co-act with the support elements of the housing for mounting the radiation transmitting wall to the housing.

2. The device according to claim 1, wherein the slots are non-linear slots.

3. The device according to claim 1, wherein each slot comprises an upwardly inclined inlet section and upright end section connecting to said inclined inlet section, wherein an angle enclosed by a central axis of the inclined inlet section and a vertical axis is situated between 15 and 75 degrees.

4. The device according to claim 3, wherein the maximum width of the inlet section exceeds the maximum width of the end section.

5. The device according to claim 3, wherein the width of the end section substantially corresponds to the outer diameter of a single element of the support elements.

6. The device according to claim 1, wherein each support element is formed by a pin protruding with respect to the inner surface of the circumferential wall of the housing and/or wherein the distance between adjacent support elements is constant.

7. The device according to claim 1, wherein a bottom segment of the housing comprises and/or accommodates at least one securing element for locking in place the radiation transmitting wall with respect to the housing.

8. The device according to claim 7, wherein the securing element is movably mounted onto a stationary support structure which is connected to the housing or makes part of the housing, wherein the securing element is configured to slide with respect to the stationary support structure over a restricted distance in a vertical direction between an unlocked state and a locked state, and wherein a terminal section of the securing element comprises a visual indicator which is visible for a user in the unlocked state and which is invisible for the user in the locked state.

9. The device according to claim 8, wherein the radiation transmitting wall at least partially covers the securing element, wherein the radiation transmitting wall entirely covers the securing element in the locked state, as seen from a front view of the device, and partially covers the securing element in the unlocked state, such that the visual indicator will be left uncovered by the radiation transmitting wall.

10. The device according to claim 7, wherein the securing element comprises at least one spring, which, in a locking condition, locks the radiation transmitting wall in place with respect to the housing, and wherein said radiation transmitting wall can be unlocked with respect to the housing by manually pressing said spring into an unlocking state, wherein the spring is accessible via an opening present in a bottom part of the securing element and/or the bottom segment of the housing.

11. The device according to claim 10, wherein a middle section of the securing element may be provided with guiding means for guiding a user's finger or tool used to press the spring into the unlocking state.

12. The device according to claim 1, wherein a resilient sealing material is present in between the housing and the radiation transmitting wall.

13. The device according to claim 1, wherein the device comprises an inner radiation transmitting wall, covering the at least one radiation unit, and an outer radiation transmitting wall, covering said inner radiation transmitting wall, and connected to the housing to close the accommodating space at least partially, wherein the inner radiation transmitting wall and the outer radiation transmitting wall are spaced apart.

14. The device according to claim 1, further comprising an inlet fan arranged adjacent to at least one channel inlet.

15. The device according to claim 1, wherein the at least one radiation transmitting wall is at least partially made of glass.

16. The device according to claim 1, wherein each radiation unit comprises a rear reflector for mounting at least one radiation source by means of at least one mounting element, and at least one front reflector positioned in front of said rear reflector and connected to said rear reflector, wherein each radiation source is positioned in front of said front reflector, and wherein the at least one front reflector comprises at least one through-hole for allowing said at least one mounting element to pass said front reflector, wherein the assembly of the rear reflector and the front reflector is mounted hingeably within the housing.

17. The device according to claim 1, wherein said support elements and said plurality of slots of the support frame are mutually arranged such that said support frame is configured to hang onto and/or to be mounted by the support elements due to gravitational forces in a self-locking manner wherein the radiation transmitting wall is locked with respect to the upright housing.

18. The device according to claim 1, wherein each of said opposing inner surfaces of the circumferential wall provided with support elements, is provided with a plurality of support elements, and/or wherein each part of the support frame configured to co-act with said plurality of support elements arranged at the same inner surface of the circumferential wall comprises the plurality of slots, wherein the number of support elements is identical to the number of slots.

19. The housing for use in a device according to claim 1, wherein the housing comprises the circumferential wall and the rear wall connected to said circumferential wall, wherein said housing defines the accommodating space, and wherein the opposing inner surfaces of the circumferential wall are provided with the support elements for mounting the radiation transmitting wall.

20. Assembly for use in the device according to claim 1, said assembly comprising the radiation transmitting wall and the support frame, directly or indirectly attached to the rear side of said radiation transmitting wall, wherein said support frame comprises the plurality of slots configured to co-act with the support elements of the housing for mounting the radiation transmitting wall to the housing of the device.

* * * * *